United States Patent
Boyd et al.

(10) Patent No.: US 10,098,824 B2
(45) Date of Patent: Oct. 16, 2018

(54) SYSTEM PROVIDING PERHYDROLASE-CATALYZED REACTION

(71) Applicants: Colgate-Palmolive Company, New York, NY (US); E.I. DU PONT DE NEMOURS AND COMPANY, Wilmington, DE (US)

(72) Inventors: Thomas Boyd, Metuchen, NJ (US); Guofeng Xu, Plainsboro, NJ (US); Richard Adams, Monmouth Junction, NJ (US); Robert Pierce, Basking Ridge, NJ (US); Derek Samaroo, Edison, NJ (US); David Viscio, Prescott Valley, AZ (US); Kari A. Fosser, Wilmington, DE (US); Robert Dicosimo, Chadds Ford, PA (US); Hong Wang, Kennett Square, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/364,738

(22) PCT Filed: Dec. 18, 2012

(86) PCT No.: PCT/US2012/070367
§ 371 (c)(1),
(2) Date: Jun. 12, 2014

(87) PCT Pub. No.: WO2013/096318
PCT Pub. Date: Jun. 27, 2013

(65) Prior Publication Data
US 2015/0265511 A1 Sep. 24, 2015

Related U.S. Application Data

(60) Provisional application No. 61/577,529, filed on Dec. 19, 2011.

(51) Int. Cl.
| | | |
|---|---|---|
| A61K 8/66 | (2006.01) | |
| A61K 8/22 | (2006.01) | |
| A61K 8/37 | (2006.01) | |
| A61C 15/04 | (2006.01) | |
| C07H 21/04 | (2006.01) | |
| A61K 8/38 | (2006.01) | |
| A61Q 11/00 | (2006.01) | |
| A61K 8/04 | (2006.01) | |
| B65D 35/22 | (2006.01) | |
| B65D 81/32 | (2006.01) | |

(52) U.S. Cl.
CPC ............... *A61K 8/38* (2013.01); *A61K 8/042* (2013.01); *A61K 8/22* (2013.01); *A61K 8/375* (2013.01); *A61K 8/66* (2013.01); *A61Q 11/00* (2013.01); *B65D 35/22* (2013.01); *B65D 81/3261* (2013.01); *A61K 2800/87* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 5,279,816 | A | 1/1994 | Church et al. |
| 5,302,375 | A | 4/1994 | Viscio |
| 5,403,549 | A | 4/1995 | McNeil et al. |
| 5,746,598 | A | 5/1998 | Fischer |
| 5,879,691 | A | 3/1999 | Sagel et al. |
| 5,891,453 | A | 4/1999 | Sagel et al. |
| 5,894,017 | A | 4/1999 | Sagel et al. |
| 5,989,526 | A | 11/1999 | Aaslyng et al. |
| 6,136,297 | A | 10/2000 | Sagel et al. |
| 6,221,341 | B1 | 4/2001 | Montgomery |
| 6,274,122 | B1 | 8/2001 | McLaughlin et al. |
| 6,379,653 | B1 | 4/2002 | Aaslyng et al. |
| 6,419,906 | B1 | 7/2002 | Xu et al. |
| 6,503,485 | B1 | 1/2003 | Allred et al. |
| 6,503,486 | B2 | 1/2003 | Xu et al. |
| 6,551,579 | B2 | 4/2003 | Sagel et al. |
| 6,669,929 | B1 | 12/2003 | Boyd et al. |
| 6,682,712 | B2 | 1/2004 | Angaiah et al. |
| 6,682,721 | B2 | 1/2004 | Kim et al. |
| 6,689,344 | B2 | 2/2004 | Chang et al. |

(Continued)

FOREIGN PATENT DOCUMENTS

| | | |
|---|---|---|
| DE | 102007036392 | 2/2009 |
| JP | H11240876 | 9/1999 |

(Continued)

OTHER PUBLICATIONS

International Search Report and the Written Opinion issued in International Application PCT/US12/70367 dated Feb. 13, 2014. WO.
Altschul et al., "Basic Local Alignment Search Tool," J. Mol. Biol., 215:403-410 (1990).
Binz, H. et al., "Engineering novel binding proteins from nonimmunoglobulin domains," (2005) Nature Biotechnology 23, 1257-1268.
Chenna et al., "Multiple sequence alignment with the Clustal series of programs," Nucleic Acids Res 31 (13):3497-500 (2003).
Dinu et. al., "Enzyme-Based Nanoseale Composites for Use as Active Decontamination Surfaces," Adv. Funct. Mater., 20: 392-398 (2010).

(Continued)

*Primary Examiner* — Iqbal H Chowdhury

(57) ABSTRACT

Described herein are packages for storing and dispensing multi-part tooth whitening formulations, comprising a deformable material configured to form two or more sealed chambers, e.g., wherein the first chamber contains a low viscosity liquid solution comprising an enzyme having perhydrolytic activity, and the second chamber contains a peroxide source and a at least one acyl donor substrate. Particular multi-part tooth whitening formulations using this principle and methods of use thereof are also provided.

9 Claims, 2 Drawing Sheets

Specification includes a Sequence Listing.

(56) References Cited

U.S. PATENT DOCUMENTS

| | | |
|---|---|---|
| 6,705,541 B2 | 3/2004 | Schuehrer et al. |
| 6,730,316 B2 | 5/2004 | Chen |
| 6,732,887 B2 | 5/2004 | Bills et al. |
| 6,780,401 B2 | 8/2004 | Kim et al. |
| 6,893,629 B2 | 5/2005 | Prosise et al. |
| 6,949,240 B2 | 9/2005 | Sagel et al. |
| 6,956,142 B2 | 10/2005 | Bedekar et al. |
| 7,128,899 B2 | 10/2006 | Chen |
| 7,189,385 B2 | 3/2007 | Montgomery |
| 7,243,788 B2 | 7/2007 | Schmidt et al. |
| 7,510,859 B2 | 3/2009 | Wieland et al. |
| 7,552,823 B2 | 6/2009 | Schuehrer et al. |
| 7,723,083 B2 | 5/2010 | DiCosimo et al. |
| 7,754,460 B2 | 7/2010 | Amin et al. |
| 7,763,235 B2 | 7/2010 | Boyd et al. |
| 7,776,010 B2 | 8/2010 | Jessop et al. |
| 7,785,572 B2 | 8/2010 | Kim et al. |
| 7,794,378 B2 | 9/2010 | Splane, Jr. et al. |
| 7,807,141 B2 | 10/2010 | Huang et al. |
| 7,829,315 B2 | 11/2010 | DiCosimo et al. |
| 7,862,801 B2 | 1/2011 | Chen |
| 7,862,802 B2 | 1/2011 | Kim et al. |
| 7,870,952 B2 | 1/2011 | Fontana et al. |
| 7,909,165 B2 | 3/2011 | Perrel et al. |
| 7,951,566 B2 | 5/2011 | DiCosimo et al. |
| 7,964,378 B2 | 6/2011 | DiCosimo et al. |
| 8,110,536 B2 | 2/2012 | Dietshe et al. |
| 8,222,012 B2 | 7/2012 | DiCosimo et al. |
| 8,354,381 B2 | 1/2013 | Fahnestock et al. |
| 8,663,616 B2 | 3/2014 | Butterick et al. |
| 2004/0018156 A1 | 1/2004 | Szeles et al. |
| 2004/0112769 A1 | 6/2004 | Perry et al. |
| 2004/0120903 A1 | 6/2004 | Sagel et al. |
| 2005/0008526 A1 | 1/2005 | Bianchetti et al. |
| 2005/0038181 A1 | 2/2005 | Chopra et al. |
| 2005/0063923 A1 | 3/2005 | Prencipe et al. |
| 2005/0069502 A1 | 3/2005 | Chopra et al. |
| 2005/0163729 A1 | 7/2005 | Zaidel et al. |
| 2005/0249678 A1 | 11/2005 | Hassan et al. |
| 2005/0253916 A1 | 11/2005 | Poncelet et al. |
| 2005/0260544 A1 | 11/2005 | Jones et al. |
| 2005/0287084 A1 | 12/2005 | Ibrahim et al. |
| 2006/0024246 A1 | 2/2006 | Maitra et al. |
| 2006/0292092 A1 | 12/2006 | Sharma et al. |
| 2006/0292520 A1 | 12/2006 | Dillon et al. |
| 2007/0105740 A1* | 5/2007 | Dicosimo ............... A61L 2/183 510/302 |
| 2007/0128129 A1 | 6/2007 | Stehr et al. |
| 2007/0178055 A1 | 8/2007 | Buch et al. |
| 2007/0231277 A1 | 10/2007 | Sharma et al. |
| 2007/0269388 A1 | 11/2007 | Sagel et al. |
| 2008/0029130 A1* | 2/2008 | Concar ............... C11D 1/667 134/36 |
| 2008/0152600 A1 | 6/2008 | Huang et al. |
| 2008/0176299 A1 | 7/2008 | Dicosimo et al. |
| 2008/0176783 A1 | 7/2008 | Dicosimo et al. |
| 2008/0260836 A1 | 10/2008 | Boyd et al. |
| 2009/0005590 A1 | 1/2009 | Dicosimo et al. |
| 2009/0311198 A1 | 12/2009 | Concar et al. |
| 2010/0041752 A1 | 2/2010 | Dicosimo et al. |
| 2010/0059394 A1 | 3/2010 | Fontana et al. |
| 2010/0086534 A1 | 4/2010 | DiCosimo et al. |
| 2010/0086535 A1 | 4/2010 | DiCosimo et al. |
| 2010/0087529 A1 | 4/2010 | Dicosimo et al. |
| 2010/0136639 A1 | 6/2010 | DiCosimo et al. |
| 2010/0196287 A1 | 8/2010 | O'Connell et al. |
| 2010/0247589 A1 | 9/2010 | Fahnestock et al. |
| 2011/0081693 A1 | 4/2011 | DiCosimo et al. |
| 2011/0236335 A1 | 9/2011 | DiCosimo et al. |
| 2011/0236339 A1 | 9/2011 | Dicosimo et al. |
| 2012/0288548 A1 | 11/2012 | Boyd et al. |
| 2013/0171217 A1* | 7/2013 | Chisholm ............... A61K 8/22 424/401 |
| 2014/0105948 A1 | 4/2014 | Gebreselassie et al. |
| 2014/0314829 A1 | 10/2014 | Boyd et al. |
| 2014/0338688 A1 | 11/2014 | Boyd et al. |
| 2015/0118167 A1 | 4/2015 | Boyd et al. |

FOREIGN PATENT DOCUMENTS

| | | |
|---|---|---|
| JP | 2008512372 | 4/2008 |
| JP | 2010512165 | 4/2010 |
| JP | 20125220559 | 9/2012 |
| WO | WO 1992/017158 | 10/1992 |
| WO | WO 2001/004250 | 1/2001 |
| WO | WO 2001/064175 | 9/2001 |
| WO | WO 2002/074275 | 9/2002 |
| WO | WO 2003/015656 | 2/2003 |
| WO | WO 2004/024104 | 3/2004 |
| WO | WO 2004/028500 | 4/2004 |
| WO | WO 2004/041102 | 5/2004 |
| WO | WO 2005/056782 | 6/2005 |
| WO | WO 2005/102254 | 11/2005 |
| WO | WO 2005/110344 | 11/2005 |
| WO | WO 2005/124012 | 12/2005 |
| WO | WO 2006/009737 | 1/2006 |
| WO | WO 2006/028503 | 3/2006 |
| WO | WO 2006/069236 | 6/2006 |
| WO | WO 2006/111803 | 10/2006 |
| WO | WO 2006-119060 | * 11/2006 |
| WO | WO 2007/041408 | 4/2007 |
| WO | WO 2007/103050 | 9/2007 |
| WO | WO 2008/073139 | 6/2008 |
| WO | WO 2008/140988 | 11/2008 |
| WO | WO 2009/015951 | 2/2009 |
| WO | WO-2010/039956 | * 4/2010 |
| WO | WO2010039953 | 4/2010 |
| WO | WO 2010/117753 | 10/2010 |
| WO | WO 2011/041367 | 4/2011 |
| WO | WO 2011/090980 | 7/2011 |
| WO | WO 2011/094497 | 8/2011 |
| WO | WO2012087970 | 6/2012 |
| WO | WO 2013/039495 | 3/2013 |
| WO | WO2013-096318 | * 6/2013 |
| WO | WO 2013/096321 | 6/2013 |

OTHER PUBLICATIONS

Goujon et al., "A new bioinformatics analysis tools framework at EMBL-EBI," Nucleic Acids Research (2010) 38 Suppl: W695-9.
Higgins et al., "Fast and sensitive multiple sequence alignments on a microcomputer," CABIOS, 1989, 5:151-153.
Hosse et al., "A new generation of protein display scaffolds for molecular recognition," Prot. Sci. (2006) 15(1): 14-27.
Mitsushima et al., 1995, "Gene Cloning, Nucleotide Sequence, and Expression of a Cephalosporin-C Deacetylase from Bacillus subtilis," Appl. Env. Microbiol. 61(6):2224-2229.
Muyldermans, S., "Single domain camel antibodies: current status," Rev. Mol. Biotechnol. (2001) 74:277-302.
Needleman and Wunsch, "A general method applicable to the search for similarities in the amino acid sequence of two proteins," J. Mol. Biol. 48, 443-453 (1970).
Pinkernell et al., "Simultaneous HPLC Determination of Peroxyacetic Acid and Hydrogen Peroxide," Anal. Chem., 69(17):3623-3627 (1997).
Pinkernell et. Al., "Detective Photometric Determinatoin of Peroxyearboxylic Acids in the Presence of Hydrogen Peroxide," Analyst, 122: 567-571 (1997).
Rice et al "EMBOSS: The European Molecular Biology Open Software Suite," Trends in Genetics 16, (6):276-277 (2000).
Smith-Waterman, "Identification of Common Molecular Subsequences," J. Mol. Biol. 147:195-197 (1981).
Thompson et al., "CLUSTAL W: improving the sensitivity of progressive multiple sequence alignment through sequence weighting, position-specific gap penalties and weight matrix choice," Nucleic Acids Research, 22(22):4673-4680 (1994).
Vincent et al., "Multifunctional Xylooligosaccharide/ Cephalosporin C Deacetylase Revealed by the Hexameric Structure of the Bacillus subtilis Enzyme at 1.9 A Resolution," J. Mol. Biol., 330:593-606 (2003).

(56) References Cited

OTHER PUBLICATIONS

Pearson, Comput. Methods Genome Res., [Proc. Int. Symp.] (1994), Meeting Date 1992, Editor(s): Suhai, Sandor. Publisher: Plenum, New York, NY, pp. 111-120.

Coutinho et al., "Carbohydrate-active enzymes: an integrated database approach" in Recent Advances in Carbohydrate Bioengineering, H.J. Gilbert, G. Davies, B. Henrissat and B. Svensson eds., (1999) The Royal Society of Chemistry, Cambridge, pp. 3-12.

Dong, "Cosmetics Formulation Design and Production Process $1^{st}$ Edition" China Textile & Apparel Press, 79-80 (2007).

Grachyova, Tekhonologiya fermentnyhk preparatov, 2nd Issue, revised, M.: Agropromizdat 1987, p. 149.

Nafee et al., "Mucoadhesive Delivery Systems. I. Evaluation of Mucoadhesive Polymers for Buccal Tablet Formulation," Drug Development and Industrial Pharmacy 30:985-993 (2004).

Shojaei et al., "Systemic Drug Delivery via the Buccal Mucosal Route," Pharmaceutical Technology pp. 25(6):70-81 (2001).

Smart, "Recent developments in the use of bioadhesive systems for delivery of drugs to the oral cavity," Critical Reviews in Therapeutic Drug Carrier Systems 21:319-344 (2004).

Sudhakar et al., "Buccal bioadhesive drug delivery—a promising option for orally less efficient drugs," J. Controlled Release 114(1):15-40 (2006).

STN Chemical Abstracts Registry Database, 1984, CAS Registry No. 25395-31-7.

STN Chemical Abstracts Registry Database, 1984, CAS Registry No. 102-76-1.

STN Chemical Abstracts Registry Database, 1984, CAS Registry No. 623-84-7.

STN Chemical Abstracts Registry Database, 1984, CAS Registry No. 111-55-7.

International Search Report issued in International Application No. PCT/US2011/051546, dated Jul. 16, 2012, 4 pages.

International Search Report issued in International Application PCT/US2011/65827, dated Nov. 22, 2012.

International Search Report in International Application PCT/US2012/070371, dated Feb. 13, 2014, 5 pages.

International Search Report in International Application PCT/US2012/070367, dated Feb. 13, 2014, 5 pages.

NCBI (National Center for Biotechnology Information. PubChem Compound Database; CID=31294,<https://pubchem.ncbi.nlm.nih.gov/compound/31294> (accessed Jun. 3, 2016)).

Prokhorov, Bolshaya Sovetskaya Entisiklopediya, 3rd Issue, vol. 7, M.: Soy. Entisiklopediya, 1972, p. 254.

Espacenet Abstract of JPH11240876, Hashiyama T., "Production of Optically Phenyloxirane Compound", English Version of Abstract, 2 pages.

\* cited by examiner

SYSTEM PROVIDING PERHYDROLASE-CATALYZED REACTION

CROSS-REFERENCE TO RELATED APPLICATIONS

This application claims priority to U.S. Application No. 61/577,529, filed on 19 Dec. 2011, which is hereby incorporated by reference in its entirety.

BACKGROUND

It is frequently desirable to keep formulation components separate prior to use, for example because the components may be too unstable for long-term storage if combined. It is desirable in such cases to be able to mix the formulation components at the point of use in an efficient and simple way.

One example of a formulation where it may be desirable to keep formulation components separate is tooth-whitening formulations comprising reactive ingredients such as peroxides or peroxyacids or their precursors. For example, one may want to combine A+B or A+B+C to obtain an unstable bleach X, but keep A and B separate up to that point. The difficulty arises in that during use the mixing must be rapid, and diffusion of the bleaching agent, X, to the tooth surface must be efficient. Unfortunately, combining multiple gels or other moderately viscous materials is not generally an efficient way to quickly mix chemicals; if a typical consumer were to mix by hand, it would lead to regions of well-mixed and poorly-mixed sample. One has only to hand-mix two viscous house paints together to easily see the problem: rather than efficient blending of the two colors, laminar flow causes the colors to exist in adjacent streaks. To overcome this problem directly would require more time and mixing effort than the typical user would be willing to devote to the task, and where the reactive species X begins to break down within minutes, such a method would be unworkable.

There is thus a need for products that permit ingredients to be efficiently and effectively combined at the point of use.

SUMMARY

The invention provides a multi-chamber system, wherein one chamber contains a a low viscosity liquid solution and another contains a liquid, powder or mixture of powders, the chambers being separated by a frangible or tearable barrier, such that upon squeezing one chamber, the barrier breaks and the components of the chambers can mix, to form a solution, emulsion, suspension or extrudable gel, which can be dispensed through an outlet in the second chamber, wherein the low viscosity liquid solution comprises a protein having perhydrolase activity which contains the carbohydrate esterase family 7 signature motif, and the other chamber or chambers contains an acyl donor, e.g., a carboxylic acid ester, and a peroxide source, such that upon mixing of the contents of the chambers, the protein having perhydrolase activity catalyzes a reaction between the peroxide released by the peroxide source and the acyl donor to form a peracid. Applied to the teeth, such a peracid is highly effective for bleaching the teeth, so that effective bleaching action can be achieved in a shorter period and with lower peroxide levels.

In a particular embodiment, one chamber contains a low viscosity aqueous solution comprising a protein having perhydrolytic activity (i.e., a family 7 carbohydrate esterase), and another chamber contains a gellant, a peroxide, and carboxylic acid ester compound, all in powder form, such that when the barrier is broken and the contents of the chambers allowed to mix, the peroxide and the carboxylic acid ester can react, the reaction being catalyzed by the perhydrolase, to form a peracid, in an extrudable gel formed by the liquid and the gellant, which extrudable gel can then be extruded and applied to the teeth, e.g., using a tray or strip, for sufficient time, e.g., 10-30 minutes, to allow the teeth to bleach.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE BIOLOGICAL SEQUENCES

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO: 1 is the amino acid sequence of *Thermotoga maritima* C277S variant perhydrolase.

SEQ ID NO: 2 is the amino acid sequence of fusion protein comprising the *Thermotoga maritima* C277S variant perhydrolase coupled to a tooth binding domain (also known as "EZ-7" in International Patent Application Publication No. WO2012/087970A2 to Butterick et al.).

SEQ ID NO: 3 is the nucleic acid sequence encoding a cephalosporin C deacetylase from *Bacillus subtilis* ATCC® 31954™.

SEQ ID NO: 4 is the amino acid sequence of a cephalosporin C deacetylase from *Bacillus subtilis* ATCC® 31954™.

SEQ ID NO: 5 is the amino acid sequence of a cephalosporin C deacetylase from *Bacillus subtilis* subsp. *subtilis* strain 168.

SEQ ID NO: 6 is the amino acid sequence of a cephalosporin C deacetylase from *B. subtilis* ATCC® 6633™.

SEQ ID NO: 7 is the amino acid sequence of a cephalosporin C deacetylase from *B. licheniformis* ATCC® 14580™.

SEQ ID NO: 8 is the amino acid sequence of an acetyl xylan esterase from *B. pumilus* PS213.

SEQ ID NO: 9 is the amino acid sequence of an acetyl xylan esterase from *Clostridium thermocellum* ATCC® 27405™.

SEQ ID NO: 10 is the amino acid sequence of an acetyl xylan esterase from *Thermotoga neapolitana*.

SEQ ID NO: 11 is the amino acid sequence of an acetyl xylan esterase from *Thermotoga maritima* MSB8.

SEQ ID NO: 12 is the amino acid sequence of an acetyl xylan esterase from *Thermoanaerobacterium* sp. JW/SL YS485.

SEQ ID NO: 13 is the amino acid sequence of a cephalosporin C deacetylase from *Bacillus halodurans* C-125.

SEQ ID NO: 14 is the amino acid sequence of a cephalosporin C deacetylase from *Bacillus clausii* KSM-K16.

SEQ ID NO: 15 is the amino acid sequence of a *Thermotoga neapolitana* acetyl xylan esterase variant from U.S. Patent Application Publication No. 2010-0087529 (incorporated herein by reference in its entirety), where the Xaa residue at position 277 is Ala, Val, Ser, or Thr.

SEQ ID NO: 16 is the amino acid sequence of a *Thermotoga maritima* MSB8 acetyl xylan esterase variant from U.S. Patent Application Publication No. 2010-0087529, where the Xaa residue at position 277 is Ala, Val, Ser, or Thr.

SEQ ID NO: 17 is the deduced amino acid sequence of a *Thermotoga lettingae* acetyl xylan esterase variant from U.S. Patent Application Publication No. 2010-0087529, where the Xaa residue at position 277 is Ala, Val, Ser, or Thr.

SEQ ID NO: 18 is the amino acid sequence of a *Thermotoga petrophila* acetyl xylan esterase variant from U.S. Patent Application Publication No. 2010-0087529, where the Xaa residue at position 277 is Ala, Val, Ser, or Thr.

SEQ ID NO: 19 is the amino acid sequence of a *Thermotoga* sp. RQ2 acetyl xylan esterase variant derived from "RQ2(a)" from U.S. Patent Application Publication No. 2010-0087529, where the Xaa residue at position 277 is Ala, Val, Ser, or Thr.

SEQ ID NO: 20 is the amino acid sequence of a *Thermotoga* sp. RQ2 acetyl xylan esterase variant derived from "RQ2(b)" from U.S. Patent Application Publication No. 2010-0087529, where the Xaa residue at position 278 is Ala, Val, Ser, or Thr.

SEQ ID NO: 21 is the amino acid sequence of a *Thermotoga lettingae* acetyl xylan esterase.

SEQ ID NO: 22 is the amino acid sequence of a *Thermotoga petrophila* acetyl xylan esterase.

SEQ ID NO: 23 is the amino acid sequence of a first acetyl xylan esterase from *Thermotoga* sp. RQ2 described as "RQ2(a)".

SEQ ID NO: 24 is the amino acid sequence of a second acetyl xylan esterase from *Thermotoga* sp. RQ2 described as "RQ2(b)".

SEQ ID NO: 25 is the amino acid sequence of a *Thermoanaerobacterium saccharolyticum* cephalosporin C deacetylase.

SEQ ID NO: 26 is the amino acid sequence of the acetyl xylan esterase from *Lactococcus lactis* (GENBANK® accession number ABX75634.1).

SEQ ID NO: 27 is the amino acid sequence of the acetyl xylan esterase from *Mesorhizobium loti* (GENBANK® accession number BAB53179.1).

SEQ ID NO: 28 is the amino acid sequence of the acetyl xylan esterase from *Geobacillus stearothermophilus* (GENBANK® accession number AAF70202.1).

SEQ ID NOs 29-163 are the amino acid sequences of peptides having affinity to an oral cavity surface.

SEQ ID NOs: 164-177 are the amino acid sequences of peptide linkers/spacers.

SEQ ID NOs: 178-197 are the amino acid sequences of various targeted perhydrolase fusion constructs comprising a perhydrolytic enzyme couple via a peptide linker to a binding domain having affinity for an oral surface (see International Patent Application Publication No. WO2012/087970A2 to Butterick et al.).

BRIEF DESCRIPTION OF THE DRAWINGS

The present invention will become more fully understood from the detailed description and the accompanying drawings, wherein.

DETAILED DESCRIPTION

Figure 1:
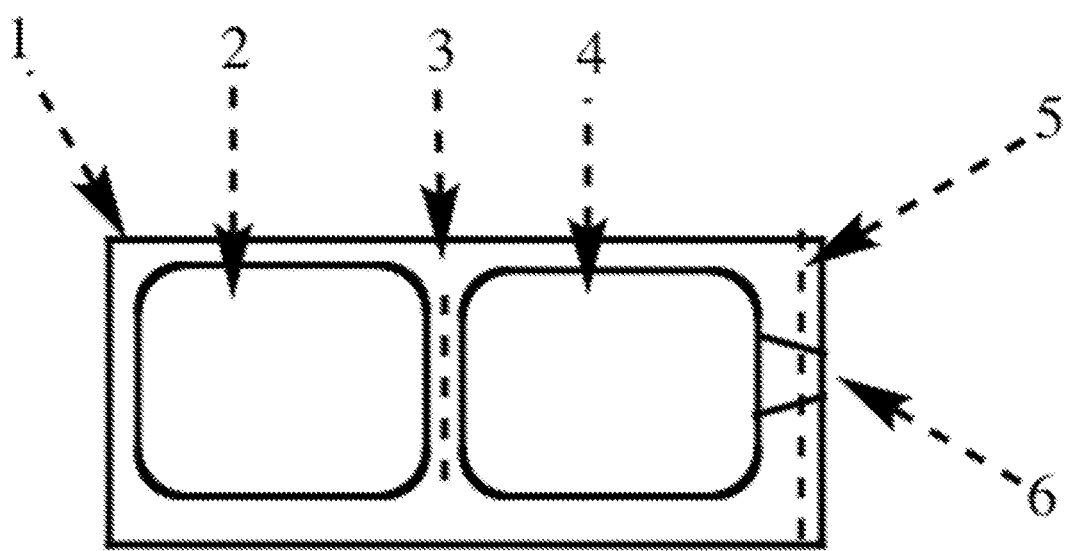
FIG. 1 depicts one embodiment of the invention which is a two-chambered package in accordance with the invention, the package being heat-sealed about the perimeter (1), and having a first chamber (2) which contains a liquid component and a second chamber (4) comprising a powder component, separated by a frangible seal (3), such that when the first chamber (2) is squeezed, the frangible seal (3) ruptures and the liquid flows into the second chamber (4) and mixes with the powder, which resulting mixture can then be dispensed by breaking the scored edge (5) to allow the mixture to flow or be squeezed out of the nozzle (6).
Figure 2:
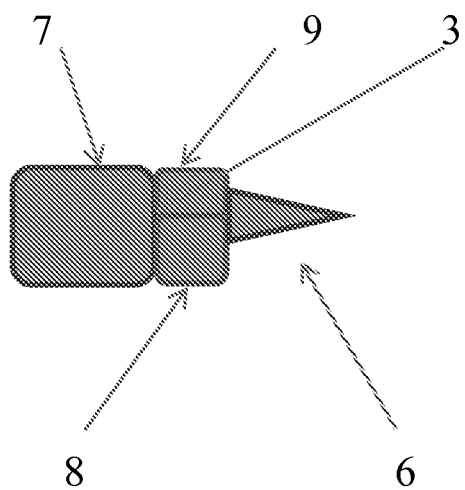
FIG. 2 depicts another embodiment of the invention, permitting mixing of components just prior to use, as described for FIG. 1, but utilizing a three-chambered package having a nozzle which can be opened by the consumer for dispensing product. In this embodiment, the package comprises a first chamber (7), a second chamber (8), a third chamber (9), the chambers being separated by frangible seals (3), and a nozzle with a break-away tip (6) to dispense the materials after mixing.

The following description of the preferred embodiment(s) is merely exemplary in nature and is in no way intended to limit the invention, its application, or uses.

As used herein, the terms "substrate", "suitable substrate", "acyl donor", and "carboxylic acid ester substrate" interchangeably refer specifically to:

(a) one or more esters having the structure $$[X]_m R_5$$

wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a cyclic five-membered heteroaromatic or six-membered cyclic aromatic or heteroaromatic moiety optionally substituted with a hydroxyl group; wherein each carbon atom in $R_5$ individually comprises no more than one hydroxyl group or no more than one ester group, and wherein $R_5$ optionally comprises one or more ether linkages;

m is an integer ranging from 1 to the number of carbon atoms in $R_5$, said one or more esters having solubility in water of at least 5 ppm at 25° C.; or (b) one or more glycerides having the structure

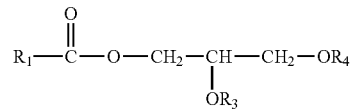

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

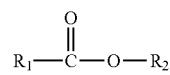

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)\text{—}O)_nH$ and n is 1 to 10; or (d) one or more acetylated monosaccharides, acetylated disaccharides, or acetylated polysaccharides; or (e) any combination of (a) through (d).

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

As used herein, the terms "acetylated sugar" and "acetylated saccharide" refer to mono-, di- and polysaccharides comprising at least one acetyl group. Examples include, but are not limited to glucose pentaacetate; xylose tetraacetate; acetylated xylan; acetylated xylan fragments; β-D-ribofuranose-1,2,3,5-tetraacetate; tri-O-acetyl-D-galactal; and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,5-pentanediol; 1,6-pentanediol; 1,2-hexanediol; 2,5-hexanediol; 1,6-hexanediol; and mixtures thereof, refer to said compounds comprising at least one ester group of the formula RC(O)O, wherein R is a C1 to C7 linear hydrocarbyl moiety. In one embodiment, the carboxylic acid ester substrate is selected from the group consisting of propylene glycol diacetate (PGDA), ethylene glycol diacetate (EDGA), and mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "suitable reaction components", "suitable aqueous reaction mixture", "reaction mixture", and "peracid-generating components" refer to the materials and water in which the reactants and the perhydrolytic enzyme catalyst come into contact. The peracid-generating components will include at least enzyme having perhydrolytic activity, wherein the perhydrolytic enzyme is at least one CE-7 perhydrolase (optionally in the form of a fusion protein targeted to a body surface), at least one suitable carboxylic acid ester substrate, a source of peroxygen, and water.

As used herein, the term "perhydrolysis" is defined as the reaction of a selected substrate with peroxide to form a peracid. Typically, inorganic peroxide is reacted with the selected substrate in the presence of a catalyst to produce the peroxycarboxylic acid. As used herein, the term "chemical perhydrolysis" includes perhydrolysis reactions in which a substrate (a peroxycarboxylic acid precursor) is combined with a source of hydrogen peroxide wherein peroxycarboxylic acid is formed in the absence of an enzyme catalyst. As used herein, the term "enzymatic perhydrolysis" includes perhydrolysis reactions in which a carboxylic acid ester substrate (a peracid precursor; the "acyl donor") is combined with a source of hydrogen peroxide and water whereby the enzyme catalyst catalyzes the formation of peracid.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peroxycarboxylic acid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (such as by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

As used herein, "acetyl xylan esterases" refers to an enzyme (E.C. 3.1.1.72; AXEs) that catalyzes the deacetylation of acetylated xylans and other acetylated saccharides.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61(6):2224-2229). The amino acid sequences of several cephalosporin C deacetylases having significant perhydrolytic activity are provided herein.

As used herein, the term "*Bacillus subtilis* ATCC® 31954™" refers to a bacterial cell deposited to the American Type Culture Collection (ATCC) having international depository accession number ATCC® 31954™. As described herein, an enzyme having significant perhydrolase activity from *B. subtilis* ATCC® 31954™ is provided as SEQ ID NO: 4 (see United States Patent Application Publication No. 2010-0041752).

As used herein, the term "*Thermotoga maritima* MSB8" refers to a bacterial cell reported to have acetyl xylan esterase activity (GENBANK® NP 227893.1; see U.S.

Patent Application Publication No. 2008-0176299). The amino acid sequence of the enzyme having perhydrolase activity from *Thermotoga maritima* MSB8 is provided as SEQ ID NO: 11. Variants of the *Thermotoga maritima* MSB8 perhydrolase are provided as SEQ ID NOs: 1 and 16.

As used herein, an "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

As used herein, an "isolated nucleic acid molecule", "isolated polynucleotide", and "isolated nucleic acid fragment" will be used interchangeably and refer to a polymer of RNA or As used herein, the terms "signature motif" and "diagnostic motif" refer to conserved structures shared among a family of enzymes having a defined activity. The signature motif can be used to define and/or identify the family of structurally-related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. In one embodiment, the perhydrolytic enzymes used in the present compositions and methods comprise a CE-7 carbohydrate esterase signature motif.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Accelrys Software Corp., San Diego, Calif.), BLASTP, BLASTN, BLASTX (Altschul et al., *J. Mol. Biol.* 215:403-410 (1990)), and DNASTAR (DNASTAR, Inc. 1228 S. Park St. Madison, Wis. 53715 USA), CLUSTALW (for example, version 1.83; Thompson et al., *Nucleic Acids Research*, 22(22):4673-4680 (1994)), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

The term "body surface" refers to any surface of the human body that may serve as the target for a benefit agent, such as a peracid benefit agent. The present methods and compositions are directed to oral care applications and products. As such, the body surface comprises an oral cavity material/surface. In one embodiment, the oral cavity material comprises tooth enamel.

As used herein, the terms "tooth whitening" and "tooth bleaching" are used interchangeably, to refer to improving the brightness (e.g., whitening) of a tooth or teeth.

As used in herein, "intrinsic stains" in teeth refer to the resulting color from chromogens within the enamel and underlying dentin. The intrinsic color of human teeth tends to become more yellow with aging, due to the thinning of the enamel and darkening of the underlying yellow dentin. Removal of intrinsic stain usually requires the use of peroxides or other oxidizing chemicals, which penetrate the enamel and decolorize the internal chromogens.

In contrast to intrinsic stains, "extrinsic stains" form on the surface of the teeth when exogenous chromogenic materials bind to the enamel, usually within the pellicle naturally coating the teeth. Most people accumulate some degree of unsightly extrinsic stains on their teeth over time. This staining process is promoted by such factors as: (1) the ingestion of tannin-containing foods and beverages such as coffee, tea, or red wine; (2) the use of tobacco products; and/or (3) exposure to certain cationic substances (e.g., tin, iron, and chlorhexidine). These substances tend to adhere to the enamel's hydroxyapatite structure, which leads to tooth discoloration and a concomitant reduction in tooth whiteness. Over a period of years, extrinsic stains may penetrate the enamel layer and result in intrinsic stains.

As used herein, the term "destain" or "destaining" refers to the process of removing a stain from an oral cavity surface. The stain(s) may be intrinsic stains, extrinsic stains, or a combination thereof.

As used herein, "effective amount of perhydrolase enzyme" refers to the quantity of perhydrolase enzyme necessary to achieve the enzymatic activity required in the specific application. Such effective amounts are readily ascertained by one of ordinary skill in the art and are based on many factors, such as the particular enzyme variant used.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the peroxygen source in the present whitening strips is in the form of granular particles, wherein the user hydrates the granular peroxide particles to release an effective amount of hydrogen peroxide. As described herein, the concentration of the hydrogen peroxide provided by the peroxygen compound in the aqueous reaction formulation is initially at least 0.1 mM or more upon combining the reaction components. In one embodiment, the hydrogen peroxide concentration in the aqueous reaction formulation is at least 0.5 mM. In one embodiment, the hydrogen peroxide concentration in the aqueous reaction formulation is at least 1 mM. In another embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g., triglyceride, ($H_2O_2$:substrate) in the formulation may be from about 0.002 to 20, preferably about 0.1 to 10, and most preferably about 0.1 to 1.

As used herein, the term "oligosaccharide" refers to compounds containing between 2 and at least 24 monosaccharide units linked by glycosidic linkages. The term "monosaccharide" refers to a compound of empirical formula $(CH_2O)_n$, where n≥3, the carbon skeleton is unbranched, each carbon atom except one contains a hydroxyl group, and the remaining carbon atom is an aldehyde or ketone at carbon atom 1. The term "monosaccharide" also refers to intracellular cyclic hemiacetal or hemiketal forms.

As used herein, the term "hydratable adhesive" will refer to an adhesive material capable of being hydrated. The hydratable adhesive is substantially dry and non-adhesive until hydrated. Upon hydration, the hydratable adhesive becomes sufficiently adhesive to bind to the surface of a tooth.

As used herein, the term "effective amount" will refer to the amount of material necessary to achieve the desired effect.

As used herein, the term "substantially non-adhesive until hydrated" will refer to the lack of adhesive strength sufficient to adhere to the surface of teeth prior to hydration.

By "sequence identity" is meant amino acid identity using a sequence alignment program, e.g., ClustalW or BLAST, e.g., generally as described in Altschul S F, Gish W, Miller W, Myers E W, Lipman D J, "Basic local alignment search tool", J Mol Biol (1990) 215 (3): 403-410, and Goujon M, McWilliam H, Li W, Valentin F, Squizzato S, Paern J, Lopez R, Nucleic Acids Research (2010) 38 Suppl: W695-9.

Acyl donors for use in the present invention, for example, to form peracids upon reaction with peroxide, are selected from one or more of (i) $C_{2-18}$ carboxylic acids, e.g $C_{2-6}$ carboxylic acids (e.g., acetic acid), including lower linear or branched alkyl carboxylic acids, optionally substituted with hydroxy and/or $C_{1-4}$ alkoxy; (ii) hydrolysable and acceptable esters thereof (e.g. mono-, di-, and tri-glycerides and acylated saccharides) and (iii) mixtures thereof. For example, acyl donors include 1,2,3-triacetoxypropane (sometimes referred to herein as triacetin or glycerin triacetate) and acylated saccharides, e.g. acetylated saccharides. In a particular embodiment, esters for this use may, for example, be esters having solubility in water of at least 5 ppm at 25° C.

The acyl donors and/or enzymes may optionally be encapsulated. There are a variety of encapsulation options well-known to the art, both natural and synthetic. Modified starches and gum Arabic are particularly well-suited since they are food grade, relatively inexpensive, quick to dissolve, and can adsorb fairly high levels of liquid oils. Any impact on the final viscosity needs to be considered.

In some embodiments, the granules comprise an antisensitivity agent capable of desensitizing the nerves or occluding dentine tubules. In some embodiments, the antisensitivity agent is selected from a potassium ion source, a silicate, a stannous ion source, a basic amino acid, a clay, and a combination thereof. In some embodiments, the potassium ion source is an orally-acceptable potassium salt and is present in an amount effective to reduce dentinal sensitivity. In some embodiments, the potassium ion source is selected from potassium chloride, potassium nitrate and a combination thereof. In some embodiments, the basic amino acid is arginine. In some embodiments, the basic amino acid is selected from arginine phosphate, arginine bicarbonate, and arginine hydrochloride. In some embodiments, the silicate is calcium silicate.

CE-7 Perhydrolases

The present compositions and method comprise enzymes having perhydrolytic activity that are structurally classified as members of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peroxycarboxylic acids from a variety of carboxylic acid ester substrates when combined with a source of peroxygen (U.S. Pat. Nos. 7,794,378; 7,951,566; 7,723,083; and 7,964,378 and U.S. Patent Application Publication Nos. 2008-0176299, 2010-0087529, 2011-0081693, and 2011-0236335 to DiCosimo et al.; each incorporated herein by reference). Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.*, 330:593-606 (2003)). Perhydrolases comprising the CE-7 signature motif ("CE-7 perhydrolases") and/or a substantially similar structure are suitable for use in the compositions and methods described herein. Means to identify substantially similar biological molecules are well known in the art (e.g., sequence alignment protocols, nucleic acid hybridizations and/or the presence of a conserved signature motif). In one aspect, the perhydrolase includes an enzyme comprising the CE-7 signature motif and at least 20%, preferably at least 30%, more preferably at least 33%, more preferably at least 40%, more preferably at least 42%, more preferably at least 50%, more preferably at least 60%, more preferably at least 70%, more preferably at least 80%, more preferably at least 90%, and most preferably at least 90%, 91%, 92%, 93%, 94%, 95%, 96%, 97%, 98%, or 99% amino acid identity to one of the sequences provided herein.

As used herein, the phrase "enzyme is structurally classified as a CE-7 enzyme", "CE-7 perhydrolase" or "structurally classified as a carbohydrate esterase family 7 enzyme" will be used to refer to enzymes having perhydrolytic activity which are structurally classified as a CE-7 carbohydrate esterase. This family of enzymes can be defined by the presence of a signature motif (Vincent et al., supra). The signature motif for CE-7 esterases comprises three conserved motifs (residue position numbering relative to reference sequence SEQ ID NO: 1; a C277S variant of the *Thermotoga maritima* perhydrolase).

Arg118-Gly119-Gln120;
Gly186-Xaa187-Ser188-Gln189-Gly190; and
His303-Glu304.

Typically, the Xaa at amino acid residue position 187 is glycine, alanine, proline, tryptophan, or threonine. Two of the three amino acid residues belonging to the catalytic triad are in bold. In one embodiment, the Xaa at amino acid residue position 187 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 272-274 of SEQ ID NO: 1) that may be used to further define a perhydrolase belonging to the CE-7 carbohydrate esterase family. In a further embodiment, the signature motif defined above may include an additional (fourth) conserved motif defined as:

Leu272-Xaa273-Asp274.

The Xaa at amino acid residue position 273 is typically isoleucine, valine, or methionine. The fourth motif includes the aspartic acid residue (bold) belonging to the catalytic triad (Ser188-Asp274-His303).

The CE-7 perhydrolases may be in the form of fusion proteins having at least one peptidic component having affinity for at least one body surface. In one embodiment, all alignments used to determine if a targeted perhydrolase (fusion protein) comprises the CE-7 signature motif will be based on the amino acid sequence of the perhydrolytic enzyme without the peptidic component having the affinity for a body surface.

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO: 1) to determine the existence of the signature motif. In one embodiment, a CLUSTAL alignment (such as CLUSTALW) using a reference amino acid sequence (as used herein the perhydrolase sequence (SEQ ID NO: 1)) is used to identify perhydrolases belonging to the CE-7 esterase family. The relative numbering of the conserved amino acid residues is based on the residue numbering of the reference amino acid sequence to account for small insertions or deletions (for example, typically five amino acids of less) within the aligned sequence.

Examples of other suitable algorithms that may be used to identify sequences comprising the present signature motif (when compared to the reference sequence) include, but are not limited to, Needleman and Wunsch (*J. Mol. Biol.* 48, 443-453 (1970); a global alignment tool) and Smith-Waterman (*J. Mol. Biol.* 147:195-197 (1981); a local alignment tool). In one embodiment, a Smith-Waterman alignment is implemented using default parameters. An example of suitable default parameters include the use of a BLOSUM62 scoring matrix with GAP open penalty=10 and a GAP extension penalty=0.5.

In one embodiment, suitable perhydrolases include enzymes comprising the CE-7 signature motif and at least 20%, preferably at least 30%, 33%, 40%, 50%, 60%, 70%, 80%, 85%, 90%, 91%, 92%, 93%, 94%, 95%, 96%, 97%, 98%, or 99% amino acid identity to SEQ ID NO: 1.

Examples of suitable CE-7 carbohydrate esterases having perhydrolytic activity include, but are not limited to, enzymes having an amino acid sequence such as SEQ ID NOs: 1, and 4-28. In one embodiment, the enzyme comprises an amino acid sequence selected from the group consisting of 1, 10, 11, 15, and 16.

As used herein, the term "CE-7 variant", "variant perhydrolase" or "variant" will refer to CE-7 perhydrolases having a genetic modification that results in at least one amino acid addition, deletion, and/or substitution when compared to the corresponding enzyme (typically the wild type enzyme) from which the variant was derived; so long as the CE-7 signature motif and the associated perhydrolytic activity are maintained. CE-7 variant perhydrolases may also be used in the present compositions and methods. Examples of CE-7 variants are provided as SEQ ID NOs: 1, 15, 16, 17, 18, 19, and 20. In one embodiment, the variants may include SEQ ID NOs: 1 and 16.

The skilled artisan recognizes that substantially similar CE-7 perhydrolase sequences (retaining the signature motifs) may also be used in the present compositions and methods. In one embodiment, substantially similar sequences are defined by their ability to hybridize, under highly stringent conditions with the nucleic acid molecules associated with sequences exemplified herein. In another embodiment, sequence alignment algorithms may be used to define substantially similar enzymes based on the percent identity to the DNA or amino acid sequences provided herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of highly stringent hybridization conditions is 0.1×SSC, 0.1% SDS, 65° C. and washed with 2×SSC, 0.1% SDS followed by a final wash of 0.1×SSC, 0.1% SDS, 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, *CABIOS*, 5:151-153 (1989); Higgins et al., *Nucleic Acids Res*. 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=−1, protein GAPDIST=4, and KTUPLE=1. In one embodiment, a fast or slow alignment is used with the default settings where a slow alignment is preferred. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

In one aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein. In another aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein. Suitable nucleic acid molecules not only have the above homologies, but also typically encode a polypeptide having about 210 to 340 amino acids in length, about 300 to about 340 amino acids, preferably about 310 to about 330 amino acids, and most preferably about 318 to about 325 amino acids in length wherein each polypeptide is characterized as having perhydrolytic activity.

Targeted Perhydrolases

As used herein, the term "targeted perhydrolase" and "targeted enzyme having perhydrolytic activity" will refer to a fusion proteins comprising at least one perhydrolytic enzyme (wild type or variant thereof) fused/coupled to at least one peptidic component having affinity for a target surface, preferably a targeted body surface. The perhydrolytic enzyme within the targeted perhydrolase may be any CE-7 carbohydrate esterase having perhydrolytic activity. The CE-7 perhydrolase may be identified by the presence of the CE-7 signature motif that aligns with a reference sequence SEQ ID NO: 1, said signature motif comprising:
 i) an RGQ motif at positions corresponding to positions 118-120 of SEQ ID NO: 1;
 ii) a GXSQG motif at positions corresponding to positions 186-190 of SEQ ID NO:1; and
 iii) an HE motif at positions corresponding to positions 303-304 of SEQ ID NO:1.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution In one embodiment, perhydrolytic enzymes may be those having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to any of the amino acid sequences reported herein (i.e., SEQ ID NOs: 1, and 4-28).

In another embodiment, the fusion protein comprises a perhydrolytic enzyme having an amino acid sequence selected from the group consisting of SEQ ID NOs: 1, and 4-28.

As used herein the terms "peptidic component", "peptidic component having affinity for an oral cavity surface", "oral cavity binding domain", and "OCBD" will refer to component of the fusion protein that is not part of the perhydrolytic enzyme comprising at least one polymer of two or more amino acids joined by a peptide bond; wherein the component has affinity for the target oral cavity surface. In a preferred aspect, the OCBD has affinity for tooth enamel.

In one embodiment, the peptidic component having affinity for a body surface may be an antibody, an Fab antibody fragment, a single chain variable fragment (scFv) antibody, a Camelidae antibody (Muyldermans, S., *Rev. Mol. Biotechnol*. (2001) 74:277-302), a non-antibody scaffold display protein (Hosse et al., *Prot. Sci*. (2006) 15(1): 14-27 and Binz, H. et al. (2005) *Nature Biotechnology* 23, 1257-1268 for a review of various scaffold-assisted approaches) or a single chain polypeptide lacking an immunoglobulin fold. In another aspect, the peptidic component having affinity for the oral cavity tissue/surface (such as tooth enamel) is a single chain peptide lacking an immunoglobulin fold.

The peptidic component having affinity for an oral cavity surface may be separated from the perhydrolytic enzyme by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. In one embodiment, at least one peptide linker is present and may be repeated up to 10 times.

In one embodiment, the fusion peptide comprises at least one oral cavity surface-binding peptide selected from the group consisting of SEQ ID NOs: 178-197.

The peptidic component having affinity for an oral cavity surface may be separated from the CE-7 perhydrolase by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. Examples of peptide linkers are provided as SEQ ID NOs: 164-177.

As such, examples of targeted CE-7 perhydrolases may include, but are not limited to, any of the CE-7 perhydrolases having an amino acid sequence selected from the group consisting of SEQ ID NOs 1, and 4-28 coupled to a peptidic component having affinity for an oral cavity surface. In a preferred embodiment, examples of targeted perhydrolases may include, but are not limited to, any of CE-7 perhydrolases having an amino acid sequence selected from the group consisting of SEQ ID NOs 1, 4, 5, 6, 7, 8, 9, 10, 11, 12, 13, 14, 15, 16, 17, 18, 19, 20, 21, 22, 23, 24, 25, 26, 27, and 28 coupled to one or more body surface-binding peptides having affinity for an oral cavity surface (optionally through a peptide spacer). In a preferred embodiment, the targeted perhydrolase includes a CE-7 perhydrolase having an amino acid sequence selected from the group consisting of SEQ ID NOs: 1 and 16.

In one embodiment, the perhydrolase is a CE-7 perhydrolase in the form of a fusion protein having the following general structure:

PAH-My-OCBD or OCBD-[L]y-PAH wherein PAH is the enzyme having perhydrolytic activity, e.g., having a CE-7 signature motif, e.g., SEQ ID NO:1, and OCBD is a peptidic component having affinity for an oral cavity surface; and L is an optional linker; and y is an integer ranging from 0 to 10. In one embodiment, the linker (L) is present and is a peptide linker ranging from 1 to 100 amino acids in length.

For example SEQ ID NO: 2 is a fusion protein having a perhydrolase sequence of SEQ ID NO: 1 coupled to a C-terminal targeting domain with an affinity for oral tissues.

The perhydrolases for use in the products and methods of the invention may be in free, protected (e.g., acetylated), or salt form.

In another embodiment, the target surface is a material that is part of the packaging and or delivery to the oral cavity. The peptidic component is selected for it affinity to a material or materials in use such as polymers, plastics and films. The targeted CE-7 perhydrolase fusion protein design allows for the controlled delivery and removal of the perhydrolase from the user by maintaining it on a removable device such as a mouth tray or strip.

Binding Affinity

The peptidic component having affinity for the oral cavity surface comprises a binding affinity for an oral cavity surface of $10^{-5}$ molar (M) or less. In certain embodiments, the peptidic component is one or more oral cavity surface-binding peptides and/or binding domain(s) having a binding affinity of $10^{-5}$ molar (M) or less for tooth enamel. In some embodiments, the binding peptides or domains will have a binding affinity value of $10^{-5}$ M or less in the presence of at least about 50-500 mM salt. The term "binding affinity" refers to the strength of the interaction of a binding peptide with its respective substrate. Binding affinity can be defined or measured in terms of the binding peptide's dissociation constant ("$K_D$"), or "$MB_{50}$."

"$K_D$" corresponds to the concentration of peptide at which the binding site on the target is half occupied, i.e., when the concentration of target with peptide bound (bound target material) equals the concentration of target with no peptide bound. The smaller the dissociation constant, the more tightly the peptide is bound. For example, a peptide with a nanomolar (nM) dissociation constant binds more tightly than a peptide with a micromolar (μM) dissociation constant. Certain embodiments of the invention will have a $K_D$ value of $10^{-5}$ or less.

"$MB_{50}$" refers to the concentration of the binding peptide that gives a signal that is 50% of the maximum signal obtained in an ELISA-based binding assay. See, e.g., Example 3 of U.S. Patent Application Publication 2005/022683; hereby incorporated by reference. The $MB_{50}$ provides an indication of the strength of the binding interaction or affinity of the components of the complex. The lower the value of $MB_{50}$, the stronger, i.e., "better," the interaction of the peptide with its corresponding substrate. For example, a peptide with a nanomolar (nM) $MB_{50}$ binds more tightly than a peptide with a micromolar (μM) $MB_{50}$. Certain embodiments of the invention will have a $MB_{50}$ value of $10^{-5}$ M or less.

In some embodiments, the peptidic component having affinity for an oral cavity surface may have a binding affinity, as measured by $K_D$ or $MB_{50}$ values, of less than or equal to about $10^{-5}$ M, less than or equal to about $10^{-6}$ M, less than or equal to about $10^{-7}$ M, less than or equal to about $10^{-8}$ M, less than or equal to about $10^{-9}$ M, or less than or equal to about $10^{-10}$ M.

In some embodiments, the oral cavity surface-binding peptides and/or oral cavity surface-binding domains may have a binding affinity, as measured by $K_D$ or $MB_{50}$ values, of less than or equal to about $10^{-5}$ M, less than or equal to about $10^{-6}$ M, less than or equal to about $10^{-7}$ M, less than or equal to about $10^{-8}$ M, less than or equal to about $10^{-9}$ M, or less than or equal to about $10^{-10}$ M.

As used herein, the term "strong affinity" will refer to a binding affinity having a $K_D$ or $MB_{50}$ value of less than or equal to about $10^{-5}$ M, preferably less than or equal to about $10^{-6}$ M, more preferably less than or equal to about $10^{-7}$ M, more preferably less than or equal to about $10^{-8}$ M, less than or equal to about $10^{-9}$ M, or most preferably less than or equal to about $10^{-10}$ M.

Enzyme Powders

In some embodiments, the personal care compositions may use an enzyme catalyst in form of a stabilized enzyme powder. Methods to make and stabilize formulations comprising an enzyme powder are described in U.S. Patent Application Publication Nos. 2010-0086534 and 2010-0086535.

In one embodiment, the enzyme may be in the enzyme powder in an amount in a range of from about 5 weight percent (wt %) to about 75 wt % based on the dry weight of the enzyme powder. A preferred weight percent range of the enzyme in the enzyme powder/spray-dried mixture is from about 10 wt % to 50 wt %, and a more preferred weight percent range of the enzyme in the enzyme powder/spray-dried mixture is from about 20 wt % to 33 wt %.

In one embodiment, the enzyme powder may further comprise an excipient. In one aspect, the excipient is provided in an amount in a range of from about 95 wt % to about 25 wt % based on the dry weight of the enzyme powder. A preferred wt % range of excipient in the enzyme powder is from about 90 wt % to 50 wt %, and a more preferred wt % range of excipient in the enzyme powder is from about 80 wt % to 67 wt %.

In one embodiment, the excipient used to prepare an enzyme powder may be an oligosaccharide excipient. In one embodiment, the oligosaccharide excipient has a number average molecular weight of at least about 1250 and a weight average molecular weight of at least about 9000. In some embodiments, the oligosaccharide excipient has a number average molecular weight of at least about 1700 and a weight average molecular weight of at least about 15000. Specific oligosaccharides may include, but are not limited to, maltodextrin, xylan, pullulan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and mixtures thereof. In a preferred embodiment, the oligosaccharide excipient is maltodextrin. Oligosaccharide-based excipients may also include, but are not limited to, water-soluble non-ionic cellulose ethers, such as hydroxymethyl-cellulose and hydroxypropylmethylcellulose, and mixtures thereof. In yet a further embodiment, the excipient may be selected from, but not limited to, one or more of the following compounds: trehalose, lactose, sucrose, mannitol, sorbitol, glucose, cellobiose, α-cyclodextrin, pullulan, and carboxymethylcellulose.

Suitable Ester Substrates/Acyl Donors

Suitable carboxylic acid ester substrates may include esters having the following formula:

(a) one or more esters having the structure $[X]_m R_5$ wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a five-membered cyclic heteroaromatic moiety or six-membered cyclic aromatic or heteroaromatic moiety optionally substituted with a hydroxyl group; wherein each carbon atom in $R_5$ individually comprises no more than one hydroxyl group or no more than one ester group or carboxylic acid group, and wherein $R_5$ optionally comprises one or more ether linkages;

m is an integer ranging from 1 to the number of carbon atoms in $R_5$, said one or more esters having solubility in water of at least 5 ppm at 25° C.; or (b) one or more glycerides having the structure

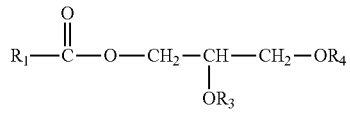

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

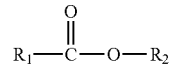

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)\text{—}O)_nH$ and n is 1 to 10; or (d) one or more acetylated monosaccharides, acetylated disaccharides, or acetylated polysaccharides; or (e) any combination of (a) through (d).

Suitable substrates may also include one or more acylated saccharides selected from the group consisting of acylated mono-, di-, and polysaccharides. In another embodiment, the acylated saccharides are selected from the group consisting of acetylated xylan; fragments of acetylated xylan; acetylated xylose (such as xylose tetraacetate); acetylated glucose (such as α-D-glucose pentaacetate; β-D-glucose pentaacetate; 1-thio-β-D-glucose-2,3,4,6-tetraacetate); β-D-galactose pentaacetate; sorbitol hexaacetate; sucrose octaacetate; β-D-ribofuranose-1,2,3,5-tetraacetate; β-D-ribofuranose-1,2,3,4-tetraacetate; tri-O-acetyl-D-galactal; tri-O-acetyl-D-glucal; β-D-xylofuranose tetraacetate, β-D-glucopyranose pentaacetate; β-D-glucopyranose-1,2,3,4-tetraacetate; β-D-glucopyranose-2,3,4,6-tetraacetate; 2-acetamido-2-deoxy-1,3,4,6-tetracetyl-β-D-glucopyranose; 2-acetamido-2-deoxy-3,4,6-triacetyl-1-chloride-α-D-glucopyranose; β-D-mannopyranose pentaacetate, and acetylated cellulose. In a preferred embodiment, the acetylated saccharide is selected from the group consisting of β-D-ribofuranose-1,2,3,5-tetraacetate; tri-O-acetyl-D-galactal; tri-O-acetyl-D-glucal; sucrose octaacetate; and acetylated cellulose.

In another embodiment, additional suitable substrates may also include 5-acetoxymethyl-2-furaldehyde; 3,4-diacetoxy-1-butene; 4-acetoxybenezoic acid; vanillin acetate; propylene glycol methyl ether acetate; methyl lactate; ethyl lactate; methyl glycolate; ethyl glycolate; methyl methoxyacetate; ethyl methoxyacetate; methyl 3-hydroxybutyrate; ethyl 3-hydroxybutyrate; and triethyl 2-acetyl citrate.

In another embodiment, suitable substrates are selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-D-glucal; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,5-pentanediol; 1,6-pentanediol; 1,2-hexanediol; 2,5-hexanediol; 1,6-hexanediol; and mixtures thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate; 1,2-propanediol diacetate; 1,4-butanediol diacetate; 1,5-pentanediol diacetate, etc.). In a further embodiment, the substrate is propylene glycol diacetate (PGDA), ethylene glycol diacetate (EGDA), or a mixture thereof.

In a further embodiment, suitable substrates are selected from the group consisting of monoacetin, diacetin, triacetin, monopropionin, dipropionin, tripropionin, monobutyrin, dibutyrin, and tributyrin. In yet another aspect, the substrate is selected from the group consisting of diacetin and triacetin. In a most preferred embodiment, the suitable substrate comprises triacetin.

The carboxylic acid ester is present at a concentration sufficient to produce the desired concentration of peroxycarboxylic acid upon enzyme-catalyzed perhydrolysis. The carboxylic acid ester need not be completely soluble in the reaction formulation, but has sufficient solubility to permit conversion of the ester by the perhydrolase catalyst to the corresponding peroxycarboxylic acid. The carboxylic acid ester is present in the reaction formulation at a concentration of 0.05 wt % to 40 wt % of the reaction formulation, preferably at a concentration of 0.1 wt % to 20 wt % of the reaction formulation, and more preferably at a concentration of 0.5 wt % to 10 wt % of the reaction formulation.

The peroxygen source is provided as granules and may include hydrogen peroxide adducts (e.g., urea-hydrogen peroxide adduct (carbamide peroxide)) perborate salts, percarbonate salts and peroxide salts. The concentration of peroxygen compound in the reaction formulation may range from 0.0033 wt % to about 50 wt %, more preferably from 0.033 wt % to about 40 wt %, and more preferably from 0.1 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor may be added to the reaction formulation. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM.

In another embodiment, the enzyme catalyst lacks significant catalase activity or may be engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis.

The concentration of peroxycarboxylic acid generated (e.g. peracetic acid) by the perhydrolysis of at least one carboxylic acid ester is at least about 0.1 ppm, preferably at least 0.5 ppm, 1 ppm, 5 ppm, 10 ppm, 20 ppm, 100 ppm, 200 ppm, 300 ppm, 500 ppm, 700 ppm, 1000 ppm, 2000 ppm, 5000 ppm or 10,000 ppm of peracid within 10 minutes, preferably within 5 minutes, of initiating the perhydrolysis reaction. Clearly one of skill in the art can adjust the reaction components to achieve the desired peracid concentration.

In one aspect, the reaction time required to produce the desired concentration of peracid is not greater than about two hours, preferably not greater than about 30 minutes, more preferably not greater than about 10 minutes, and most preferably in about 5 minutes or less.

HPLC Assay Method for Determining the Concentration of Peroxycarboxylic Acid and Hydrogen Peroxide.

A variety of analytical methods can be used to analyze the reactants and products including, but not limited to, titration, high performance liquid chromatography (HPLC), gas chromatography (GC), mass spectroscopy (MS), capillary electrophoresis (CE), the analytical procedure described by U. Pinkernell et al., (*Anal. Chem.,* 69(17):3623-3627 (1997)), and the 2,2'-azino-bis (3-ethylbenzothazoline)-6-sulfonate (ABTS) assay (U. Pinkernell et. al. *Analyst,* 122: 567-571 (1997) and Dinu et. al. *Adv. Funct. Mater.,* 20: 392-398 (2010)) as described in the present examples.

In one embodiment, the invention provides a package for an oral care product which comprises multiple chambers and is designed to keep the ingredients in each chamber separate and non-reactive until the point of use. For example, this invention provides a chemically-stable structural package design which permits an enzyme catalyzed tooth whitening product to reach pre-steady state kinetics in milliseconds after the ingredients are exposed to each other and mixed. The contents of the container are dispensed via an opening means, e.g., through a nozzle with a removable cap or plug or which becomes functional when a preferentially scored section of the container is broken off by the consumer, permitting clean and convenient dispensing of product through a shaped nozzle.

Each chamber has the capacity to store, e.g., 0.1-30 grams of an ingredient. The oral care product is a tooth whitening product providing a total quantity of product delivered from all chambers, e.g., between 1.0 to 5.0 grams, for example 1-2 grams to provide the intended benefit. The volumetric capacity of the chambers is designed to accommodate ingredients with a specific gravity of e.g., 1.0 to 1.1 and preferably with a specific gravity range of 1.02 to 1.05.

In one embodiment, the package is manufactured using a thermoforming process of at least two flexible films with a thickness of 50 micron to 500 micron and preferably 300 micron thick. The two films may be opaque, translucent or transparent and can be any combination when assembled in the thermoforming process. Both materials provide water vapor barrier characteristics, e.g., with less than 3% moisture loss over a three year time frame, e.g., less than 1% moisture loss over the same period. The films also provide flavor barrier. The flavor loss can be determined both by gas chromatography and by organoleptic evaluation.

The films are chemically resistant to the materials comprised therein. For example, in one embodiment they are resistant to 0.1% to 10% hydrogen peroxide solution by weight, e.g. up to 0.3% hydrogen peroxide solution by weight.

In one embodiment, one of the two flexible materials is a polymeric laminate and the inner layer of the laminate has been selected to bond with the first flexible material but will delaminate when pressure is manually applied to the chamber with a frangible seal. The force required to break the seal is manually applied and can vary between 2 inch-lbf and 5 inch-lbf.

After the frangible seal between the compartments are broken, the ingredients in each chamber will come into intimate contact with each other. The consumer is permitted to mix the individual ingredients for a period of time to exceed the pre-steady state kinetic rate or the burst phase. The time for pre-steady state kinetics or burst phase can be in milliseconds. This provides sufficient time for the formation and consumption of enzyme-substrate intermediates until their steady state concentrations are reached. After steady state has been achieved, the consumer can break a preferentially scored section of the multi chamber container and dispense the mixture onto a dental tray. The tray is applied to the teeth for a period of time of 15 minutes to 45 minutes and provides an effective whitening benefit.

Exemplary embodiments of the invention thus include for example packages, oral care compositions, and methods of whitening teeth, e.g.:

1. Package 1, a package comprising a deformable material configured to form at least two sealed chambers, having a first chamber, a second chamber, and optionally additional chambers, the chambers being separated by one or more barriers which are frangible or tearable, wherein the first chamber contains a low viscosity liquid solution comprising an enzyme having perhydrolytic activity, said enzyme having a carbohydrate esterase family 7 (CE-7) signature motif that aligns with a reference sequence SEQ ID NO: 1, said signature motif comprising:
  i) an RGQ motif at positions corresponding to positions 118-120 of SEQ ID NO: 1;
  ii) a GXSQG motif at positions corresponding to positions 186-190 of SEQ ID NO:1; and
  iii) an HE motif at positions corresponding to positions 303-304 of SEQ ID NO:1; and the second chamber comprises at least one acyl donor substrate, said substrate selected from the group consisting of:
  i) esters having the structure

wherein X=an ester group of the formula $R_6C(O)O$
  $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
  $R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
  M is an integer ranging from 1 to the number of carbon atoms in $R_5$; and
  wherein said esters have solubility in water of at least 5 ppm at 25° C.;
  ii) glycerides having the structure

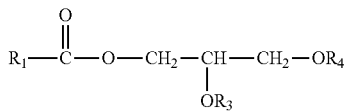

wherein $R_1$=C1 to C7 straight chain or branched chain alkyl optionally substituted with an hydroxyl or a C1 to C4 alkoxy group and $R_3$ and $R_4$ are individually H or $R_1C(O)$;
  iii) one or more esters of the formula

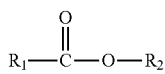

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; and
  iv) acetylated saccharides selected from the group consisting of acetylated monosaccharides, acetylated disaccharides, and acetylated polysaccharide; and wherein the second or optional additional chamber contains a peroxide source, such that when one or more barriers between the chambers breaks, e.g., upon squeezing the first chamber, the low viscosity liquid solution mixes with the peroxide source and the acyl donor substrate, and the enzyme having perhydrolytic activity catalyzes a reaction between the peroxide released by the peroxide source and the acyl donor substrate to form a peracid; and the package has an opening means, for example a scored region, cap or plug to allow opening of the package, to provide an outlet through which the mixture can be dispensed.

1.1. Package 1 wherein the enzyme having perhydrolytic activity comprises an amino acid sequence selected from:
  a) SEQ ID NO: 1; and
  b) an amino acid sequence having at least 80% amino acid sequence identity to SEQ ID NO: 1.

Package 1 or 1.1 wherein the enzyme having perhydrolytic activity further comprises a binding domain fused to the N- or C-terminus of the enzyme, said binding domain having affinity for an oral tissue or for the tooth whitening strip.

1.2. Any of the foregoing packages wherein the binding domain having affinity for an oral tissue comprises an amino acid sequence selected from the group consisting of SEQ D NOs: 178-197.

1.3. Any of the foregoing packages wherein the enzyme having perhydrolytic activity has affinity for an oral tissue and comprises an amino acid sequence selected from SEQ ID NO: 2 and an amino acid sequence having at least 80% amino acid sequence identity to SEQ ID NO: 2.

1.4. Any of the foregoing packages wherein the deformable material is plastic or aluminum.

1.5. Any of the foregoing packages wherein the low viscosity liquid solution has a viscosity sufficiently low to ensure efficient mixing with the contents of the second chamber, e.g., below 5,000 cps, e.g. below 500 cps.

1.6. Any of the foregoing packages wherein the low viscosity liquid solution comprises a buffer.

1.7. Any of the foregoing packages wherein the acyl donor substrate is selected from (i) one or more $C_{2-18}$ carboxylic acids, e.g $C_{2-6}$ carboxylic acids (e.g., acetic acid), including lower linear or branched alkyl carboxylic acids, optionally substituted with hydroxy and/or $C_{1-4}$ alkoxy; (ii) one or more hydrolysable and acceptable esters thereof (e.g. mono-, di-, and tri-glycerides and acylated saccharides) and (iii) mixtures thereof.

1.8. Any of the foregoing packages wherein the acyl donor substrate is selected from 1,2,3-triacetoxypropane (sometimes referred to herein as triacetin or glycerin triacetate) and acylated saccharides, e.g. acetylated saccharides.

1.9. Any of the foregoing packages comprising an acyl donor substrate which comprises an ester compound having solubility in water of at least 5 ppm at 25° C.

1.10. Any of the foregoing packages wherein the peroxide source is selected from solid peroxides and solid peroxide donors and mixtures thereof, e.g., selected from peroxide salts or complexes (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate); hypochlorites; urea peroxide; hydrogen peroxide polymer complexes such as hydrogen peroxide-polyvinyl pyrrolidone polymer complexes; metal peroxides e.g. zinc peroxide and calcium peroxide; for example a solid peroxide selected from urea peroxide, polyvinylpyrrolidone-hydrogen peroxide complexes, sodium percarbonate, sodium perborate, and metal peroxides e.g. zinc peroxide and calcium peroxide.

1.11. The foregoing package wherein the peroxide source is urea peroxide.
1.12. The foregoing package wherein the peroxide source comprises a hydrogen peroxide-polyvinylpyrrolidone complex.
1.13. Any of the foregoing packages wherein the ingredients of the chambers are present in amounts sufficient to provide, upon mixing, a bleaching agent in an amount and concentration effective to whiten teeth.
1.14. Any of the foregoing packages wherein the second chamber contains a gellant in powder form.
1.15. The foregoing package wherein the gellant is selected from carbomer gellants (e.g., Carbopol 971P), polysaccharide gums, such as xanthan gum, modified food starches, animal or fish-based gelatin, and silicas.
1.16. The foregoing package wherein the gellant is a carbomer gellant.
1.17. Any of the foregoing packages wherein the second chamber contains a gellant in powder form in a relative amount to provide a viscosity of 100,000 to 150,000 cps, e.g., about 125,000 cps, upon mixing with the contents of the first chamber, e.g., wherein the gellant is present in amounts of from 5% to 50% by weight of the final mixture of the contents of the first and second chambers.
1.18. Any of the foregoing packages wherein the first chamber contains a low viscosity aqueous solution comprising an enzyme having perhydrolytic activity and a buffer, and the second chamber contains a gellant, a peroxide source, and an acetyl-containing compound, all in powder form, such that when the frangible barrier is broken and the contents of the two chambers allowed to mix, the peroxide and the acetyl containing compound can react, the reaction being catalyzed by the protein having perhydrolase activity, to form peracetic acid, in an extrudable gel formed by the liquid and the gellant, which extrudable gel can then be extruded and applied to the teeth, e.g., using a tray or strip, for sufficient time, e.g., 10-30 minutes, to allow the teeth to bleach.
1.19. Any of the foregoing packages which further comprises an applicator device such as a dental tray or strip for applying a mixture of the contents of the first and second chambers to the teeth.
1.20. The foregoing package wherein, when the mixture is dispensed, the opening from the second chamber is directly attached to a tray so that the mixture is extruded into the tray.
2. Composition 2, being a multi-part oral care composition comprising a first part which is physically separated from the second part during storage and combined with the second part just prior to use, e.g., within 10 minutes of use, wherein the first part comprises an enzyme having perhydrolytic activity as described for any of the foregoing packages, and second part comprises a peroxide source and a carboxy donor selected from carboxylic acids and acyl compounds, wherein the peroxide source and the carboxy donor react in the presence of the perhydrolase to form a peracid, e.g., a peroxide source and a carboxy donor as described for any of the foregoing packages, e.g.,
 2.1. The foregoing composition wherein the carboxy donor is selected from $C_{2-18}$ carboxylic acids (e.g., acetic acid), and hydrolysable and acceptable esters thereof (e.g. mono-, di-, and tri-glycerides) and mixtures thereof
 2.2. The foregoing composition wherein the carboxy donor is 1,2,3-triacetoxypropane (sometimes referred to herein as triacetin or glycerin triacetate).
 2.3. Any of the foregoing compositions wherein the peroxide source is a solid peroxide selected from urea peroxide, polyvinylpyrrolidone-hydrogen peroxide complexes, sodium percarbonate, sodium perborate, and metal peroxides e.g. zinc peroxide and calcium peroxide.
 2.4. Any of the foregoing compositions wherein the peroxide source is urea peroxide.
 2.5. Any of the foregoing compositions wherein the peroxide source comprises a hydrogen peroxide-polyvinylpyrrolidone complex.
 2.6. Any of the foregoing compositions when packaged in a package as hereinbefore described, e.g. Package 1 et seq.
3. A method (Method 3) of whitening teeth comprising activating a two part oral care composition as hereinbefore described, by combining the two parts, and applying an effective amount of the mixture thus obtained to the teeth, e.g., using an applicator, for example a dental tray or a strip, for a sufficient time, e.g., at least 10 minutes, for example 10-30 minutes, to whiten the teeth.

Peroxycarboxylic acids ("peracids") are known as effective antimicrobial and bleaching agents. U.S. Pat. No. 5,302,375 to Viscio, D., discloses oral compositions for whitening comprising peracetic acid dissolved in a vehicle, wherein the peracetic acid is generated within the vehicle in situ by combining water, acetylsalicylic acid, and a water soluble alkali metal percarbonate. U.S. Pat. No. 5,279,816 to Church et al. discloses the use of a composition comprising peracetic acid to whiten stained or discolored teeth. U.S. Pat. Nos. 6,221,341 and 7,189,385 to Montgomery, R., disclose peroxy acid tooth-whitening compositions suitable for use in a method to whiten teeth. More specifically, a peracetic acid composition may be produced by combining a hydrogen peroxide precursor, an acetic acid ester of glycerin, and water to generate, via chemical perhydrolysis, peracetic acid.

Enzymatic perhydrolysis is not described in these references. U.S. Patent Application Publication No. 2009-0311198 to Concar et al. discloses an oral composition comprising a *M. smegmatis* enzyme having perhydrolytic activity to bleach teeth.

Many hydrolases and esterases, for example, lipases, serine hydrolases and carbohydrate esterases, catalyze perhydrolysis, the reversible formation of peracids from carboxylic acids and hydrogen peroxide. Perhydrolases, esterases, and lipases generally contain a catalytic triad consisting of a serine (Ser), a glutamate (Glu) or aspartate (Asp), and a histidine (His). Many perhydrolases (e.g. metal-free haloperoxidases) contain a Ser-His-Asp catalytic triad and catalyze the reversible formation of peracid from hydrogen peroxide and carboxylic acids. Without being bound by theory, it is believed that perhydrolysis takes place with an esterase-like mechanism in which a carboxylic acid reacts with the active site serine to form an acyl enzyme intermediate, which then reacts with hydrogen peroxide to form a peracid.

Numerous perhydrolases have been described in the art. The inclusion of specific variant subtilisin Carlsberg proteases having perhydrolytic activity in a body care product is disclosed in U.S. Pat. No. 7,510,859 to Wieland et al. Perhydrolytic enzymes beyond the specific variant proteases are not described nor are there any working examples demonstrating the enzymatic production of peracid as a personal care benefit agent. U.S. Patent Application Publication Nos. 2008-0176783 A1; 2008-0176299 A1; 2009-0005590 A1; and 2010-0041752 A1 to DiCosimo et al. disclose enzymes structurally classified as members of the CE-7 family of carbohydrate esterases (i.e., cephalosporin C deacetylases [CAHs] and acetyl xylan esterases [AXEs]) that are characterized by significant perhydrolytic activity for converting carboxylic acid ester substrates (in the presence of a suitable source of peroxygen, such as hydrogen peroxide) into peroxycarboxylic acids at concentrations sufficient for use as a disinfectant and/or a bleaching agent. Some members of the CE-7 family of carbohydrate esterases have been demonstrated to have perhydrolytic activity sufficient to produce 4000-5000 ppm peracetic acid from acetyl esters of alcohols, diols, and glycerols in 1 minute and up to 9000 ppm between 5 minutes and 30 minutes once the reaction components were mixed (DiCosimo et al., U.S. 2009-0005590 A1). U.S. Patent application publication No. 2010-0087529 A1 describes variant CE-7 enzymes having improved perhydrolytic activity.

In one embodiment, the invention uses a perhydrolase which contains the catalytic domain of a member of the carbohydrate esterase family 7 having perhydrolytic activity ("CE-7 perhydrolase"). Although the CE-7 perhydrolases have exceptional perhydrolytic activity, their use in cosmetic personal care products has not been disclosed prior to the aforementioned provisional application.

Acyl donors in the present invention are selected from (i) one or more $C_{2-18}$ carboxylic acid esters, e.g $C_{2-6}$ carboxylic acid esters, including lower linear or branched alkyl carboxylic acids, optionally substituted with hydroxy and/or $C_{1-4}$ alkoxy and (ii) mixtures thereof. For example, acyl donors include 1,2,3-triacetoxypropane (sometimes referred to herein as triacetin or glycerin triacetate) and acylated saccharides, e.g. acetylated saccharides. In a particular embodiment, esters for this use may, for example, be esters having solubility in water of at least 5 ppm at 25° C.

The acyl donors or other materials may optionally be encapsulated. There are a variety of encapsulation options well-known to the art, both natural and synthetic. Modified starches and gum arabic are particularly well-suited since they are food grade, relatively inexpensive, quick to dissolve, and can adsorb fairly high levels of liquid oils. Any impact on the final viscosity needs to be considered.

As noted above, the invention may comprise gellants, for example carbomer gellants (e.g., Carbopol 971P), polysaccharide gums, such as xanthan gum, modified food starches, animal or fish-based gelatin, and silicas. Adhesive gel formulations for use with tooth whitening agents are known in the art, e.g. as described in U.S. Pat. Nos. 7,862,801; 5,746,598; 6,730,316; 7,128,899. The gellant is useful to thicken whitening solutions to a point where they will not run out of a dental tray or away from the teeth to soft tissue areas. This allows the bleaching agent to stay in contact with the teeth for extended periods of time and protects soft tissues. The use of a dental tray and a viscous bleach allows a low concentration bleach to effectively whiten a person's teeth over a 1-2 week period of time with minimal risk to the patient. Gellants for this use should be selected and adjusted to provide a viscosity upon application of 100,000 to 150,000 cps, e.g., about 125,000 cps, In a particular embodiment, the package or multi-part composition as hereinbefore described comprises a carbomer gellant, for example a modified polyacrylic acid hydrophilic polymer such as CARBOPOL® manufactured by Lubrizol. Carbomers are capable of forming viscous gels at concentrations above as little as 5% by weight.

All ingredients for use in the formulations described herein should be orally acceptable. By "orally acceptable" as the term is used herein is meant an ingredient which is present in the formulation as described in an amount and form which does not render the formulation unsafe for use in the oral cavity.

In some embodiments, the enzyme having perhydrolytic activity comprises an amino acid sequence selected from: a) SEQ ID NO: 1; and b) an amino acid sequence having at least 80% amino acid sequence identity to SEQ ID NO: 1.

In some embodiments, the enzyme having perhydrolytic activity further comprises a binding domain fused to the N- or C-terminus of the enzyme, said binding domain having affinity for an oral tissue.

In some embodiments, the enzyme having perhydrolytic activity has affinity for an oral tissue and comprises an amino acid sequence selected from: a) SEQ ID NO: 2, and b) an amino acid sequence having at least 80% amino acid sequence identity to SEQ ID NO: 2.

In some embodiments, the immobilized enzyme is adsorbed to the insoluble material, trapped in insoluble beads, covalently bonded to the insoluble material through a chemical reaction, attached by binding domain of the peptide having affinity for the insoluble material, or entrapped in an insoluble matrix.

Some embodiments provide a method of whitening the teeth or treating gingivitis, dental plaque or halitosis, comprising preparing a liquid comprising whitening agent in accordance with the method of the preceding claim, and administering the liquid to the oral cavity, e.g., by rinsing the mouth with the liquid for a period of 15 seconds to one minute and then expectorating the liquid.

In some embodiments, the product delivers a bleaching agent in a mouthwash, wherein the bleaching agent is a peracid produced by enzyme catalyzed reaction of hydrogen peroxide and triacetin. In some embodiments, two compositions—one comprising hydrogen peroxide and the other comprising triacetin—are kept in the mouthwash bottle (first compartment). Some embodiments comprise—on top of the bottle—a second compartment that is connected, e.g., using insert or screw type joints. In some embodiments, the second compartment is, e.g. a flow through cartridge, which contains an enzyme having perhydroolytic activity immobilized onto the surfaces of carried materials, such as hydroxyapatite or cellulose particles. In some embodiments, the second compartment serves as the activation component of the mouth wash.

In some embodiments, the hydrogen peroxide and triacetin are separated from the enzyme having perhydrolytic activity. In some embodiments, during use, the mixture flows through the cartridge and comes in contact with the enzyme having perhydrolytic activity on the surfaces, and the reaction is catalyzed to produce a peracid quickly. In some embodiments—after use—the mixture is separated again from the enzyme.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

In a two-chambered package, 1.0 mL of pH 7 phosphate buffer containing 0.04 mg perhydrolase enzyme is stored separately from a multi-component powder. The multi-component powder is illustrated in Tables 1A, 1B, and 1C, and comprises the encapsulated triacetin & flavor, granular urea peroxide, and a carbomer gellant. The ratio of well-blended powders, 1A:1B:1C, in this example is 92.3:1.7:6. The two chambers are separated with a water impermeable heat-sealed barrier which is less strong than the outer seals around the package (see e.g. FIG. 1). To prepare for use, the consumer presses on the buffer/enzyme chamber, which breaks the frangible internal seal and pushes the buffer/enzyme into the powder chamber. The powders rapidly mix with the liquid, dissolving the peroxide source, the starch with adsorbed triacetin & flavor, and, more slowly, hydrating the gellant. After several seconds of mixing these components, the gel has effectively formed, and is ready to be applied to a tray. Approximately 0.5 grams of the newly-formed gel is applied to both an upper and lower delivery device, yielding a dose of 4.3 mg urea peroxide (equivalent to 1.5 mg hydrogen peroxide), 10 mg triacetin, and 0.01 mg hydrolase enzyme.

Opening a hole in the package, via a pre-scored opening (see FIG. 1), the user can apply the gel to a tray, and then wear the tray for 20-30 minutes. Alternatively, the gel can be applied to a flexible strip such as a non-porous flexible polyethylene or a slowly dissolvable film.

TABLE 1A

Encapsulated triacetin

| Ingredient | Weight % |
|---|---|
| Starch (CAPSUL ®, National Starch) | 94.6 |
| Triacetin | 4.3 |
| Flavor | 1.1 |
| Total | 100 |

TABLE 1B

Peroxide

| Ingredient | Weight % |
|---|---|
| Urea peroxide granules, 5-10 microns | 100 |

TABLE 1C

Solid Gellant

| Ingredient | Weight % |
|---|---|
| Carbomer gellant (CARBOPOL ® 971P, Lubrizol) | 100 |

Example 2

An exemplary perhydrolytic enzyme was immobilized on a solid permeable matrix. The matrix was loaded into a syringe and a solution comprising hydrogen peroxide and triacetin were pushed through the matrix to generate and dispense peracetic acid (PAA).

The prototype enzyme matrix was prepared as follows: 0.1 g of hydroxyapatite powder was incubated with 1500 microliters of 5 micromolar enzyme having a perhydrolytic region and a hydroxyapatite binding domain, in 10 mM phosphate buffer hH 7.2 for 1 hour at 37° C. The powder was then washed 3× with 1 ml of 10 mM phosphate buffer, each time spinning down, pipetting out liquid, resuspending in buffer, and repeating. The powder was then resuspended in 500 microliters of 10 mM phosphate buffer and loaded into a 3 ml syringe with a 25 m syringe filter tip (5 micron membrane), and excess liquid was dispensed through the filter.

500 microliters of reaction buffer comprising 100 mM phosphate buffer, 100 mM triacetan, and 100 mM hydrogen peroxide was loaded into the syringe, dispensed through the filter, and collected. 90 microliters of product was collected, then the reaction was stopped with 40 microliters of 1.3M $H_3PO_4$. The resulting mixture was then diluted 1:10 in phosphate buffer and added to detection reagent, incubated 10 minutes and read at $A_{405}$ nm. The proportion of PAA generated was measured. The procedure was then repeated without enzyme, as a control.

Approximately 900 ppm of PAA was generated by this method, compared to 32 ppm without the perhydrolase enzyme. The reactants were in contact with the immobilized enzyme for less than 60 seconds:

TABLE 2A

| Sample | PAA (ppm) | Standard Deviation |
|---|---|---|
| Enzyme | 903.818 | 122.922 |
| No Enzyme | 32.438 | 2.414 |

The experiment was repeated, three times with enzyme, three times without; allowing no more than 15 seconds contact with enzyme. PAA was produced consistently at levels of ca. 300-350 ppm with enzyme, and about 65 ppm without. The results are described below in Table 2B.

TABLE 2B

| Sample | PAA (ppm) | Standard Deviation |
|---|---|---|
| Enzyme 1 | 363.380 | 74.462 |
| Enzyme 2 | 356.309 | 43.188 |
| Enzyme 3 | 308.960 | 55.096 |
| No Enzyme 1 | 66.066 | 2.663 |
| No Enzyme 2 | 63.299 | 0.533 |
| No Enzyme 3 | 65.759 | 0.533 |

Similar results were obtained using a larger (10 ml) syringe:

TABLE 2C

| Sample | PAA (ppm) | Standard Deviation |
|---|---|---|
| Enzyme | 333.864 | 65.987 |
| No Enzyme | 62.223 | 1.399 |

The reaction in the presence of the immobilized enzyme thus proceeds reproduceably, rapidly and efficiently, to provide levels of PAA which are many times the levels needed to kill bacteria, and would be sufficient to whiten teeth.

The invention claimed is:

1. A composition comprising a first part which is physically separated from a second part during storage and combined with a second part just prior to use,
wherein the first part comprises an aqueous solution of an enzyme having perhydrolase activity, which is not a proteolytic enzyme, and wherein the enzyme comprises SEQ ID NO: 1; and
wherein the second part comprises a solid peroxide source,
wherein the solid peroxide source is selected from urea peroxide, polyvinylpyrrolidone-hydrogen peroxide complexes, sodium percarbonate, sodium perborate, metal peroxides, zinc peroxide and calcium peroxide; a gellant, and at least one carboxy donor, wherein the carboxy donor is 1,2,3-triacetoxypropane, and
wherein the peroxide source and the carboxy donor in the second part are sufficiently mixed with the enzyme having perhydrolase activity in the first part upon said combination to form a peracid prior to use: and
wherein the material in the second part is in the form of a powder; and wherein the composition is a multi-part oral care composition.

2. The oral care composition according to claim 1 wherein the peroxide source is urea peroxide.

3. The multi-part oral care composition of claim 1, wherein the second part contains the gellant in powder form, such that upon mixing and formation of the peracid, an extrudable gel is formed by the liquid and the gellant, comprising the peracid, which extrudable gel can then be extruded and applied to a tooth surface, for sufficient time to whiten a tooth;

wherein the gellant is selected from a carbomer gellant, a polysaccharide gum, a modified food starch, an animal or fish-based gelatin, a silica; and a combination of two or more thereof.

4. The multi-part oral care composition of claim 1 wherein the enzyme having perhydrolase activity has affinity to oral tissue.

5. The multi-part oral care composition of claim 1, wherein the solid peroxide source is a polyvinylpyrrolidone-hydrogen peroxide complex.

6. The multi-part oral care composition of claim 1, wherein the viscosity of the aqueous solution in the first part is less than 5,000 cps.

7. The multi-part oral care composition of claim 1, wherein the viscosity of the aqueous solution in the first part is less than 500 cps.

8. The multi-part oral care composition of claim 1, wherein the gellant in the second part is present in an amount sufficient to provide a viscosity of 100,000 to 150,000 cps for the composition upon mixing with the contents of the first part prior to use.

9. A method of whitening teeth comprising
   a. activating a package composition according to claim 1 by combining the materials in the different chambers or parts respectively; and
   b. applying an effective amount of the mixture thus obtained to the teeth for a sufficient time to whiten the teeth.

\* \* \* \* \*

SEQUENCE LISTING

<160> NUMBER OF SEQ ID NOS: 197

<210> SEQ ID NO 1
<211> LENGTH: 325
<212> TYPE: PRT
<213> ORGANISM: Thermotoga maritima

<400> SEQUENCE: 1

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Gly Ser Gln Gly Gly Gly
        180                 185                 190

Ile Ala Leu Ala Val Ser Ala Leu Ser Lys Lys Ala Lys Ala Leu Leu
    195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 2
<211> LENGTH: 375
<212> TYPE: PRT
<213> ORGANISM: artificial sequence
<220> FEATURE:

<223> OTHER INFORMATION: synthetic construct
<220> FEATURE:
<221> NAME/KEY: MISC_FEATURE
<222> LOCATION: (1)..(325)
<223> OTHER INFORMATION: Thermotoma maritima C277S variant perhydrolase
<220> FEATURE:
<221> NAME/KEY: MISC_FEATURE
<222> LOCATION: (326)..(375)
<223> OTHER INFORMATION: Oral surface targeting domain

<400> SEQUENCE: 2

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Thr Lys Pro Pro Arg Thr Pro Thr Ala
            340                 345                 350

Asn Thr Ser Arg Pro His His Asn Phe Gly Ser Gly Gly Gly Gly Ser
```

```
                355                 360                 365

Pro His His His His His
    370                 375

<210> SEQ ID NO 3
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 3 atg caa cta ttc gat ctg ccg ctc gac caa ttg caa aca tat aag cct     48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg     96
Glu Lys Thr Ala Pro Lys Asp Phe Ser Glu Phe Trp Lys Leu Ser Leu
            20                  25                  30 gag gaa ctt gca aaa gtc caa gca gaa cct gat tta cag ccg gtt gac    144
Glu Glu Leu Ala Lys Val Gln Ala Glu Pro Asp Leu Gln Pro Val Asp
        35                  40                  45 tat cct gct gac gga gta aaa gtg tac cgt ctc aca tat aaa agc ttc    192
Tyr Pro Ala Asp Gly Val Lys Val Tyr Arg Leu Thr Tyr Lys Ser Phe
    50                  55                  60 gga aac gcc cgc att acc gga tgg tac gcg gtg cct gac aag caa ggc    240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat    288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca    336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att    384
Phe Gly Met Leu Val Arg Gly Gln Gln Ser Ser Glu Asp Thr Ser Ile
        115                 120                 125 tca ctg cac ggt cac gct ttg ggc tgg atg acg aaa gga att ctt gat    432
Ser Leu His Gly His Ala Leu Gly Trp Met Thr Lys Gly Ile Leu Asp
    130                 135                 140 aaa gat aca tac tat tac cgc ggt gtt tat ttg gac gcc gtc cgc gcg    480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt    528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg    576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc    624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa    672
Asn Phe Glu Arg Ala Ile Asp Val Ala Leu Glu Gln Pro Tyr Leu Glu
    210                 215                 220 atc aat tcc ttc ttc aga aga aat ggc agc ccg gaa aca gaa gtg cag    720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga    768
Ala Met Lys Thr Leu Ser Tyr Phe Asp Ile Met Asn Leu Ala Asp Arg
                245                 250                 255
```

-continued

```
gtg aag gtg cct gtc ctg atg tca atc ggc ctg att gac aag gtc acg    816
Val Lys Val Pro Val Leu Met Ser Ile Gly Leu Ile Asp Lys Val Thr
    260                 265                 270 ccg ccg tcc acc gtg ttt gcc gcc tac aat cat ttg gaa aca gag aaa    864
Pro Pro Ser Thr Val Phe Ala Ala Tyr Asn His Leu Glu Thr Glu Lys
275                 280                 285 gag ctg aag gtg tac cgc tac ttc gga cat gag tat atc cct gct ttt    912
Glu Leu Lys Val Tyr Arg Tyr Phe Gly His Glu Tyr Ile Pro Ala Phe
    290                 295                 300 caa acg gaa aaa ctt gct ttc ttt aag cag cat ctt aaa ggc tga taa    960
Gln Thr Glu Lys Leu Ala Phe Phe Lys Gln His Leu Lys Gly
305                 310                 315
```

<210> SEQ ID NO 4
<211> LENGTH: 318
<212> TYPE: PRT
<213> ORGANISM: Bacillus subtilis

<400> SEQUENCE: 4

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285
```

Glu Leu Lys Val Tyr Arg Tyr Phe Gly His Glu Tyr Ile Pro Ala Phe
290                 295                 300

Gln Thr Glu Lys Leu Ala Phe Phe Lys Gln His Leu Lys Gly
305                 310                 315

<210> SEQ ID NO 5
<211> LENGTH: 318
<212> TYPE: PRT
<213> ORGANISM: Bacillus subtilis

<400> SEQUENCE: 5

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
                20                  25                  30

Glu Glu Leu Ala Lys Val Gln Ala Glu Pro Asp Leu Gln Pro Val Asp
            35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Thr
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Gln Pro Tyr Leu Glu
210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Lys Lys
        275                 280                 285

Glu Leu Lys Val Tyr Arg Tyr Phe Gly His Glu Tyr Ile Pro Ala Phe
290                 295                 300

Gln Thr Glu Lys Leu Ala Phe Phe Lys Gln His Leu Lys Gly
305                 310                 315

<210> SEQ ID NO 6
<211> LENGTH: 318
<212> TYPE: PRT
<213> ORGANISM: Bacillus subtilis

<400> SEQUENCE: 6

```
Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315
```

<210> SEQ ID NO 7
<211> LENGTH: 318
<212> TYPE: PRT
<213> ORGANISM: Bacillus licheniformis

<400> SEQUENCE: 7

```
Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45
```

Glu Tyr Pro Ala Asp Gly Val Lys Val Tyr Trp Leu Thr Tyr Arg Ser
                50                  55                  60

Ile Gly Gly Ala Arg Ile Lys Gly Trp Tyr Ala Val Pro Asp Arg Gln
 65                  70                  75                  80

Gly Pro His Pro Ala Ile Val Lys Tyr His Gly Tyr Asn Ala Ser Tyr
                             85                  90                  95

Asp Gly Asp Ile His Asp Ile Val Asn Trp Ala Leu His Gly Tyr Ala
                100                 105                 110

Ala Phe Gly Met Leu Val Arg Gly Gln Asn Ser Ser Glu Asp Thr Glu
                115                 120                 125

Ile Ser His His Gly His Val Pro Gly Trp Met Thr Lys Gly Ile Leu
130                 135                 140

Asp Pro Lys Thr Tyr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175

Gly Val Ile Gly Ala Ser Gln Gly Gly Leu Ala Val Ala Val Ser
                180                 185                 190

Ala Leu Ser Asp Ile Pro Lys Ala Ala Val Ser Glu Tyr Pro Tyr Leu
                195                 200                 205

Ser Asn Phe Gln Arg Ala Ile Asp Thr Ala Ile Asp Gln Pro Tyr Leu
210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
                260                 265                 270

Thr Pro Pro Ser Thr Val Phe Ala Ala Tyr Asn His Leu Glu Thr Asp
                275                 280                 285

Lys Glu Ile Lys Val Tyr Arg Tyr Phe Gly His Glu Tyr Ile Pro Pro
                290                 295                 300

Phe Gln Thr Glu Lys Leu Ala Phe Leu Arg Lys His Leu Lys
305                 310                 315

<210> SEQ ID NO 8
<211> LENGTH: 320
<212> TYPE: PRT
<213> ORGANISM: Bacillus pumilus

<400> SEQUENCE: 8

Met Gln Leu Phe Asp Leu Ser Leu Glu Glu Leu Lys Lys Tyr Lys Pro
 1               5                  10                  15

Lys Lys Thr Ala Arg Pro Asp Phe Ser Asp Phe Trp Lys Lys Ser Leu
                20                  25                  30

Glu Glu Leu Arg Gln Val Glu Ala Glu Pro Thr Leu Glu Ser Tyr Asp
                35                  40                  45

Tyr Pro Val Lys Gly Val Lys Val Tyr Arg Leu Thr Tyr Gln Ser Phe
 50                  55                  60

Gly His Ser Lys Ile Glu Gly Phe Tyr Ala Val Pro Asp Gln Thr Gly
 65                  70                  75                  80

Pro His Pro Ala Leu Val Arg Phe His Gly Tyr Asn Ala Ser Tyr Asp
                 85                  90                  95

Gly Gly Ile His Asp Ile Val Asn Trp Ala Leu His Gly Tyr Ala Thr

```
                100              105                110
Phe Gly Met Leu Val Arg Gly Gln Gly Ser Glu Asp Thr Ser Val
            115              120              125
Thr Pro Gly Gly His Ala Leu Gly Trp Met Thr Lys Gly Ile Leu Ser
            130              135              140
Lys Asp Thr Tyr Tyr Tyr Arg Gly Val Tyr Leu Asp Ala Val Arg Ala
145              150              155              160
Leu Glu Val Ile Gln Ser Phe Pro Glu Val Asp Glu His Arg Ile Gly
            165              170              175
Val Ile Gly Gly Ser Gln Gly Gly Ala Leu Ala Ile Ala Ala Ala
            180              185              190
Leu Ser Asp Ile Pro Lys Val Val Ala Asp Tyr Pro Tyr Leu Ser
            195              200              205
Asn Phe Glu Arg Ala Val Asp Val Ala Leu Glu Gln Pro Tyr Leu Glu
            210              215              220
Ile Asn Ser Tyr Phe Arg Arg Asn Ser Asp Pro Lys Val Glu Glu Lys
225              230              235              240
Ala Phe Glu Thr Leu Ser Tyr Phe Asp Leu Ile Asn Leu Ala Gly Trp
            245              250              255
Val Lys Gln Pro Thr Leu Met Ala Ile Gly Leu Ile Asp Lys Ile Thr
            260              265              270
Pro Pro Ser Thr Val Phe Ala Ala Tyr Asn His Leu Glu Thr Asp Lys
            275              280              285
Asp Leu Lys Val Tyr Arg Tyr Phe Gly His Glu Phe Ile Pro Ala Phe
            290              295              300
Gln Thr Glu Lys Leu Ser Phe Leu Gln Lys His Leu Leu Ser Thr
305              310              315              320

<210> SEQ ID NO 9
<211> LENGTH: 320
<212> TYPE: PRT
<213> ORGANISM: Clostridium thermocellum

<400> SEQUENCE: 9

Met Ala Gln Leu Tyr Asp Met Pro Leu Glu Glu Leu Lys Lys Tyr Lys
1               5                10               15
Pro Ala Leu Thr Lys Gln Lys Asp Phe Asp Glu Phe Trp Glu Lys Ser
            20               25               30
Leu Lys Glu Leu Ala Glu Ile Pro Leu Lys Tyr Gln Leu Ile Pro Tyr
            35               40               45
Asp Phe Pro Ala Arg Arg Val Lys Val Phe Arg Val Glu Tyr Leu Gly
        50               55               60
Phe Lys Gly Ala Asn Ile Glu Gly Trp Leu Ala Val Pro Glu Gly Glu
65               70               75               80
Gly Leu Tyr Pro Gly Leu Val Gln Phe His Gly Tyr Asn Trp Ala Met
            85               90               95
Asp Gly Cys Val Pro Asp Val Val Asn Trp Ala Leu Asn Gly Tyr Ala
            100              105              110
Ala Phe Leu Met Leu Val Arg Gly Gln Gln Gly Arg Ser Val Asp Asn
            115              120              125
Ile Val Pro Gly Ser Gly His Ala Leu Gly Trp Met Ser Lys Gly Ile
            130              135              140
Leu Ser Pro Glu Glu Tyr Tyr Tyr Arg Gly Val Tyr Met Asp Ala Val
145              150              155              160
```

```
Arg Ala Val Glu Ile Leu Ala Ser Leu Pro Cys Val Asp Glu Ser Arg
                165                 170                 175
Ile Gly Val Thr Gly Gly Ser Gln Gly Gly Gly Leu Ala Leu Ala Val
            180                 185                 190
Ala Ala Leu Ser Gly Ile Pro Lys Val Ala Val His Tyr Pro Phe
            195                 200                 205
Leu Ala His Phe Glu Arg Ala Ile Asp Val Ala Pro Asp Gly Pro Tyr
    210                 215                 220
Leu Glu Ile Asn Glu Tyr Leu Arg Arg Asn Ser Gly Glu Glu Ile Glu
225                 230                 235                 240
Arg Gln Val Lys Lys Thr Leu Ser Tyr Phe Asp Ile Met Asn Leu Ala
                245                 250                 255
Pro Arg Ile Lys Cys Arg Thr Trp Ile Cys Thr Gly Leu Val Asp Glu
            260                 265                 270
Ile Thr Pro Pro Ser Thr Val Phe Ala Val Tyr Asn His Leu Lys Cys
            275                 280                 285
Pro Lys Glu Ile Ser Val Phe Arg Tyr Phe Gly His Glu His Met Pro
    290                 295                 300
Gly Ser Val Glu Ile Lys Leu Arg Ile Leu Met Asp Glu Leu Asn Pro
305                 310                 315                 320

<210> SEQ ID NO 10
<211> LENGTH: 325
<212> TYPE: PRT
<213> ORGANISM: Thermotoga neapolitana

<400> SEQUENCE: 10

Met Ala Phe Phe Asp Met Pro Leu Glu Glu Leu Lys Lys Tyr Arg Pro
1               5                   10                  15
Glu Arg Tyr Glu Glu Lys Asp Phe Asp Glu Phe Trp Arg Glu Thr Leu
                20                  25                  30
Lys Glu Ser Glu Gly Phe Pro Leu Asp Pro Val Phe Glu Lys Val Asp
            35                  40                  45
Phe His Leu Lys Thr Val Glu Thr Tyr Asp Val Thr Phe Ser Gly Tyr
    50                  55                  60
Arg Gly Gln Arg Ile Lys Gly Trp Leu Leu Val Pro Lys Leu Ala Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Met Lys Gly Asp
        115                 120                 125
Thr Pro Asp Tyr Pro Glu Gly Pro Val Asp Pro Gln Tyr Pro Gly Phe
    130                 135                 140
Met Thr Arg Gly Ile Leu Asp Pro Gly Thr Tyr Tyr Tyr Arg Arg Val
145                 150                 155                 160
Phe Val Asp Ala Val Arg Ala Val Glu Ala Ala Ile Ser Phe Pro Arg
                165                 170                 175
Val Asp Ser Arg Lys Val Val Ala Gly Ser Gln Gly Gly Gly
            180                 185                 190
Ile Ala Leu Ala Val Ser Ala Leu Ser Asn Arg Val Lys Ala Leu Leu
        195                 200                 205
Cys Asp Val Pro Phe Leu Cys His Phe Arg Arg Ala Val Gln Leu Val
    210                 215                 220
```

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Val Pro Ala Leu Phe Ser Val Gly Leu
        260                 265                 270

Met Asp Thr Ile Cys Pro Pro Ser Thr Val Phe Ala Ala Tyr Asn His
    275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 11
<211> LENGTH: 325
<212> TYPE: PRT
<213> ORGANISM: Thermotoga maritima

<400> SEQUENCE: 11

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Ala Lys Ala Leu Leu
    195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu

```
            260                 265                 270
Met Asp Asn Ile Cys Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 12
<211> LENGTH: 320
<212> TYPE: PRT
<213> ORGANISM: Thermoanaerobacterium sp.

<400> SEQUENCE: 12

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Val Arg Gly Gln Gly Gly Gln Ser Gln Asp Val Gly Gly
        115                 120                 125

Val Thr Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Gly Leu Ser Leu Ala Cys Ala
            180                 185                 190

Ala Leu Glu Pro Arg Val Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300
```

```
Arg Gly Phe Gly Asp Leu Ala Met Gln Phe Met Leu Glu Leu Tyr Ser
305                 310                 315                 320
```

<210> SEQ ID NO 13
<211> LENGTH: 319
<212> TYPE: PRT
<213> ORGANISM: Bacillus halodurans

<400> SEQUENCE: 13

```
Met Pro Leu Ile Asp Met Pro Leu Thr Glu Leu Lys Glu Tyr Met Gly
1               5                   10                  15

Arg Asn Pro Lys Pro Asp Asp Phe Thr Glu Tyr Trp Asp Arg Ala Leu
                20                  25                  30

Gln Glu Met Arg Lys Val Asn Pro Asn Val Glu Leu Ile Pro Ser Asp
            35                  40                  45

Phe Gln Thr Thr Tyr Ala Glu Cys Phe His Leu Tyr Phe Thr Gly Val
    50                  55                  60

Arg Gly Ala Arg Ile His Ala Lys Tyr Val Arg Pro Arg His Thr Ser
65                  70                  75                  80

Gly Thr His Pro Ala Val Ile His Phe His Gly Tyr Thr Met Asn Ala
                85                  90                  95

Gly Glu Trp Thr Gly Leu Leu His Tyr Ala Ala Leu Gly Tyr Ser Val
            100                 105                 110

Leu Ala Met Asp Val Arg Gly Gln Gly Gly Leu Ser Glu Asp Thr Gly
        115                 120                 125

Gly Val Lys Gly Asn Thr His Ser Gly His Ile Ile Arg Gly Leu Asp
    130                 135                 140

Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175

Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
        195                 200                 205

Leu Ser Asp Tyr Gln Arg Val Trp Glu Met Asp Leu Ala Glu Lys Ala
    210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Ala Val Gly Leu Met
            260                 265                 270

Asp Thr Val Cys Pro Pro Ser Thr Gln Phe Ala Met Tyr Asn Lys Leu
        275                 280                 285

Thr Thr Thr Lys Ser Ile Glu Leu Tyr Pro Asp Phe Ala His Glu Asp
    290                 295                 300

Leu Pro Gly His Arg Asp Arg Ile Phe Gln Phe Leu Ser Asp Leu
305                 310                 315
```

<210> SEQ ID NO 14
<211> LENGTH: 317
<212> TYPE: PRT
<213> ORGANISM: Bacillus clausii

<400> SEQUENCE: 14

Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Phe Tyr Tyr Arg Ser Ala
    50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Gly Arg Ser Ala
                85                  90                  95

Glu Trp Ser Ser Leu Leu Asn Tyr Val Ala Ala Gly Phe Ser Val Phe
                100                 105                 110

Tyr Met Asp Val Arg Gly Gln Gly Gly Thr Ser Glu Asp Pro Gly Gly
            115                 120                 125

Val Arg Gly Asn Thr Tyr Arg Gly His Ile Ile Arg Gly Leu Asp Ala
        130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205

Ser Asp Tyr Lys Arg Val Trp Gln Met Asp Leu Ala Val Arg Ser Tyr
210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
            260                 265                 270

Thr Glu Cys Pro Pro Ser Thr Gln Phe Ala Ala Tyr Asn Lys Ile Lys
        275                 280                 285

Ala Lys Lys Ser Tyr Glu Leu Tyr Pro Asp Phe Gly His Glu His Leu
    290                 295                 300

Pro Gly Met Asn Asp His Ile Phe Arg Phe Phe Thr Ser
305                 310                 315

<210> SEQ ID NO 15
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 15

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp

```
                35                  40                  45
Phe His Leu Lys Thr Val Glu Thr Tyr Asp Val Thr Phe Ser Gly Tyr
 50                  55                  60

Arg Gly Gln Arg Ile Lys Gly Trp Leu Leu Val Pro Lys Leu Ala Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
            115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Gly Ser Gln Gly Gly Gly
                180                 185                 190

Ile Ala Leu Ala Val Ser Ala Leu Ser Asn Arg Val Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 16
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 16

Met Ala Phe Phe Asp Leu Pro Leu Glu Glu Leu Lys Lys Tyr Arg Pro
 1               5                  10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
 50                  55                  60
```

```
Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
             85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
                180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 17
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 17

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80
```

```
Gly Lys Leu Pro Cys Val Val Glu Phe Val Gly Tyr Gly Gly Arg
            85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
            115                 120                 125

Thr Pro Asp Tyr Glu Asp Asn Pro Ser Asp Pro Gln Tyr Pro Gly Phe
            130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
            195                 200                 205

Cys Asp Val Pro Phe Leu Cys His Tyr Lys Arg Ala Val Gln Ile Thr
210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
            245                 250                 255

Asn Phe Ala Ala Arg Ala Lys Cys Pro Ala Leu Phe Ser Val Gly Leu
            260                 265                 270

Met Asp Asp Ile Xaa Pro Pro Ser Thr Val Phe Ala Ala Tyr Asn Tyr
            275                 280                 285

Tyr Ala Gly Glu Lys Asp Ile Arg Ile Tyr Pro Tyr Asn Asn His Glu
            290                 295                 300

Gly Gly Gly Ser Phe His Thr Leu Glu Lys Leu Lys Phe Val Lys Lys
305                 310                 315                 320

Thr Ile Ser Met Arg Glu
            325

<210> SEQ ID NO 18
<211> LENGTH: 325
<212> TYPE: PRT
<213> ORGANISM: Thermotoga petrophilia
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 18

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
            85                  90                  95

Gly Phe Pro His Asp Trp Leu Phe Trp Pro Ser Met Gly Tyr Ile Cys
```

```
                        100             105                 110
Phe Val Met Asp Thr Arg Gly Gln Gly Ser Gly Trp Met Lys Gly Asp
                115                 120                 125

Thr Pro Asp Tyr Pro Glu Asp Pro Val Asp Pro Gln Tyr Pro Gly Phe
            130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 19
<211> LENGTH: 325
<212> TYPE: PRT
<213> ORGANISM: Thermotoga sp. RQ2a
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 19

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Val Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125
```

```
Thr Pro Asp Tyr Pro Glu Asp Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 20
<211> LENGTH: 329
<212> TYPE: PRT
<213> ORGANISM: Thermotoga sp. RQ2b
<220> FEATURE:
<221> NAME/KEY: MISC_FEATURE
<222> LOCATION: (278)..(278)
<223> OTHER INFORMATION: Xaa is Ala, Val, Ser, or Thr.

<400> SEQUENCE: 20

Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
130                 135                 140
```

Phe Met Thr Arg Gly Ile Leu Asp Pro Arg Thr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Xaa Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Leu Arg Phe Met Lys
305                 310                 315                 320

Arg Ile Leu Lys Gly Glu Phe Lys Ala
                325

<210> SEQ ID NO 21
<211> LENGTH: 326
<212> TYPE: PRT
<213> ORGANISM: Thermotoga lettingae

<400> SEQUENCE: 21

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

```
Ile Ala Leu Ala Val Ser Ala Leu Ser Ser Lys Val Met Ala Leu Leu
            195                 200                 205

Cys Asp Val Pro Phe Leu Cys His Tyr Lys Arg Ala Val Gln Ile Thr
210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
            245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
            275                 280                 285

Tyr Ala Gly Glu Lys Asp Ile Arg Ile Tyr Pro Tyr Asn Asn His Glu
            290                 295                 300

Gly Gly Gly Ser Phe His Thr Leu Glu Lys Leu Lys Phe Val Lys Lys
305                 310                 315                 320

Thr Ile Ser Met Arg Glu
            325

<210> SEQ ID NO 22
<211> LENGTH: 325
<212> TYPE: PRT
<213> ORGANISM: Thermotoga petrophilia

<400> SEQUENCE: 22

Met Ala Phe Phe Asp Leu Pro Leu Glu Glu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
            115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
```

```
            225                 230                 235                 240
Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 23
<211> LENGTH: 325
<212> TYPE: PRT
<213> ORGANISM: Thermotoga sp. RQ2

<400> SEQUENCE: 23

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270
```

```
Met Asp Asn Ile Cys Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 24
<211> LENGTH: 329
<212> TYPE: PRT
<213> ORGANISM: Thermotoga sp. RQ2

<400> SEQUENCE: 24

Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Cys Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320
```

Arg Ile Leu Lys Gly Glu Phe Lys Ala
            325

<210> SEQ ID NO 25
<211> LENGTH: 320
<212> TYPE: PRT
<213> ORGANISM: Thermoanaerobacterium saccharolyticum

<400> SEQUENCE: 25

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asp Arg Ala Leu
            20                  25                  30

Asp Glu Met Arg Ser Val Asp Pro Lys Ile Lys Met Lys Lys Ser Ser
        35                  40                  45

Phe Gln Val Pro Phe Ala Glu Cys Tyr Asp Leu Tyr Phe Thr Gly Val
    50                  55                  60

Arg Gly Ala Arg Ile His Ala Lys Tyr Ile Arg Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Ala Arg Gly Gln Gly Gln Ser Gln Asp Val Gly Gly
        115                 120                 125

Val Asn Gly Asn Thr Leu Asn Gly His Ile Ile Arg Gly Leu Asp Asp
130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Gly Leu Ser Leu Ala Cys Ala
            180                 185                 190

Ala Leu Glu Pro Lys Ile Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 26
<211> LENGTH: 312
<212> TYPE: PRT
<213> ORGANISM: Lactococcus lactis

<400> SEQUENCE: 26

Met Thr Lys Ile Asn Asn Trp Gln Asp Tyr Gln Gly Ser Ser Leu Lys
1               5                   10                  15

Pro Glu Asp Phe Asp Lys Phe Trp Glu Lys Ile Asn Leu Val Ser
            20                  25                  30

Asn His Gln Phe Glu Phe Glu Leu Ile Glu Lys Asn Leu Ser Ser Lys
            35                  40                  45

Val Val Asn Phe Tyr His Leu Trp Phe Thr Ala Ile Asp Gly Ala Lys
50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
            115                 120                 125

Met Thr Met Lys Gly Leu Ile Val Arg Gly Ile Asp Glu Gly Tyr Glu
130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
            195                 200                 205

Arg Lys Ala Tyr Glu Leu Gly Ala Glu Glu Ser Ala Phe Glu Glu Leu
210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
            275                 280                 285

Ser Leu Tyr Val Leu Pro Glu Tyr Gly His Glu Tyr Leu Pro Lys Ile
290                 295                 300

Ser Asp Trp Leu Arg Glu Asn Gln
305                 310

<210> SEQ ID NO 27
<211> LENGTH: 323
<212> TYPE: PRT
<213> ORGANISM: Mesorhizobium loit

<400> SEQUENCE: 27

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
            35                  40                  45

Thr Thr Leu Lys Ala Val Gln Ser Phe Asp Val Thr Phe Pro Gly Tyr

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
130                 135                 140

Arg Gly Val Leu Asp Lys Asn Asp Tyr Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
        290                 295                 300

Gln Gly Tyr Gln Glu Arg Gln Gln Met Thr Trp Leu Ser Arg Leu Phe
305                 310                 315                 320

Gly Val Gly

<210> SEQ ID NO 28
<211> LENGTH: 329
<212> TYPE: PRT
<213> ORGANISM: Geobacillus stearothermophilus

<400> SEQUENCE: 28

Met Phe Asp Met Pro Leu Ala Gln Leu Gln Lys Tyr Met Gly Thr Asn
1               5                   10                  15

Pro Lys Pro Ala Asp Phe Ala Asp Phe Trp Ser Arg Ala Leu Glu Glu
                20                  25                  30

Leu Ser Ala Gln Ser Leu His Tyr Glu Leu Ile Pro Ala Thr Phe Gln
            35                  40                  45

Thr Thr Val Ala Ser Cys Tyr His Leu Tyr Phe Thr Gly Val Gly Gly
        50                  55                  60

Ala Arg Val His Cys Gln Leu Val Lys Pro Arg Glu Gln Lys Gln Lys
65                  70                  75                  80

Gly Pro Gly Leu Val Trp Phe His Gly Tyr His Thr Asn Ser Gly Asp
                85                  90                  95

Trp Val Asp Lys Leu Ala Tyr Ala Ala Ala Gly Phe Thr Val Leu Ala

```
                100             105             110
Met Asp Cys Arg Gly Gln Gly Gly Lys Ser Glu Asp Asn Leu Gln Val
            115                 120                 125
Lys Gly Pro Thr Leu Lys Gly His Ile Ile Arg Gly Ile Glu Asp Pro
    130                 135                 140
Asn Pro His His Leu Tyr Tyr Arg Asn Val Phe Leu Asp Thr Val Gln
145                 150                 155                 160
Ala Val Arg Ile Leu Cys Ser Met Asp His Ile Asp Arg Glu Arg Ile
                165                 170                 175
Gly Val Tyr Gly Ala Ser Gln Gly Gly Ala Leu Ala Leu Ala Cys Ala
            180                 185                 190
Ala Leu Glu Pro Ser Val Val Lys Ala Val Val Leu Tyr Pro Phe
        195                 200                 205
Leu Ser Asp Tyr Lys Arg Ala Gln Glu Leu Asp Met Lys Asn Thr Ala
    210                 215                 220
Tyr Glu Glu Ile His Tyr Tyr Phe Arg Phe Leu Asp Pro Thr His Glu
225                 230                 235                 240
Arg Glu Glu Glu Val Phe Tyr Lys Leu Gly Tyr Ile Asp Ile Gln Leu
                245                 250                 255
Leu Ala Asp Arg Ile Cys Ala Asp Val Leu Trp Ala Val Ala Leu Glu
            260                 265                 270
Asp His Ile Cys Pro Pro Ser Thr Gln Phe Ala Val Tyr Asn Lys Ile
        275                 280                 285
Lys Ser Lys Lys Asp Met Val Leu Phe Tyr Glu Tyr Gly His Glu Tyr
    290                 295                 300
Leu Pro Thr Met Gly Asp Arg Ala Tyr Leu Phe Phe Cys Pro Ile Phe
305                 310                 315                 320
Phe Pro Ile Gln Lys Arg Asn Val Lys
                325

<210> SEQ ID NO 29
<211> LENGTH: 20
<212> TYPE: PRT
<213> ORGANISM: artificial sequence
<220> FEATURE:
<223> OTHER INFORMATION: Synthetic construct

<400> SEQUENCE: 29

Ala His Pro Glu Ser Leu Gly Ile Lys Tyr Ala Leu Asp Gly Asn Ser
1               5                   10                  15

Asp Pro His Ala
            20

<210> SEQ ID NO 30
<211> LENGTH: 20
<212> TYPE: PRT
<213> ORGANISM: artificial sequence
<220> FEATURE:
<223> OTHER INFORMATION: Synthetic construct

<400> SEQUENCE: 30

Ala Ser Val Ser Asn Tyr Pro Pro Ile His His Leu Ala Thr Ser Asn
1               5                   10                  15

Thr Thr Val Asn
            20

<210> SEQ ID NO 31
<211> LENGTH: 14
```

```
<212> TYPE: PRT
<213> ORGANISM: artificial sequence
<220> FEATURE:
<223> OTHER INFORMATION: Synthetic construct

<400> SEQUENCE: 31

Asp Glu Cys Met Glu Pro Leu Asn Ala Ala His Cys Trp Arg
1               5                   10

<210> SEQ ID NO 32
<211> LENGTH: 14
<212> TYPE: PRT
<213> ORGANISM: artificial sequence
<220> FEATURE:
<223> OTHER INFORMATION: Synthetic construct

<400> SEQUENCE: 32

Asp Glu Cys Met His Gly Ser Asp Val Glu Phe Cys Thr Ser
1               5                   10

<210> SEQ ID NO 33
<211> LENGTH: 14
<212> TYPE: PRT
<213> ORGANISM: artificial sequence
<220> FEATURE:
<223> OTHER INFORMATION: Synthetic construct

<400> SEQUENCE: 33

Asp Leu Cys Ser Met Gln Met Met Asn Thr Gly Cys His Tyr
1               5                   10

<210> SEQ ID NO 34
<211> LENGTH: 14
<212> TYPE: PRT
<213> ORGANISM: artificial sequence
<220> FEATURE:
<223> OTHER INFORMATION: Synthetic construct

<400> SEQUENCE: 34

Asp Leu Cys Ser Ser Pro Ser Thr Trp Gly Ser Cys Ile Arg
1               5                   10

<210> SEQ ID NO 35
<211> LENGTH: 20
<212> TYPE: PRT
<213> ORGANISM: artificial sequence
<220> FEATURE:
<223> OTHER INFORMATION: Synthetic construct

<400> SEQUENCE: 35

Asp Pro Asn Glu Ser Asn Tyr Glu Asn Ala Thr Thr Val Ser Gln Pro
1               5                   10                  15

Thr Arg His Leu
            20

<210> SEQ ID NO 36
<211> LENGTH: 20
<212> TYPE: PRT
<213> ORGANISM: artificial sequence
<220> FEATURE:
<223> OTHER INFORMATION: Synthetic construct

<400> SEQUENCE: 36

Glu Pro Thr His Pro Thr Met Arg Ala Gln Met His Gln Ser Leu Arg
1               5                   10                  15

Ser Ser Ser Pro
```

<210> SEQ ID NO 37
<211> LENGTH: 20
<212> TYPE: PRT
<213> ORGANISM: artificial sequence
<220> FEATURE:
<223> OTHER INFORMATION: Synthetic construct

<400> SEQUENCE: 37

Gly Asn Thr Asp Thr Thr Pro Pro Asn Ala Val Met Glu Pro Thr Val
1               5                   10                  15

Gln His Lys Trp
            20

<210> SEQ ID NO 38
<211> LENGTH: 15
<212> TYPE: PRT
<213> ORGANISM: artificial sequence
<220> FEATURE:
<223> OTHER INFORMATION: Synthetic construct

<400> SEQUENCE: 38

Asn Gly Pro Asp Met Val Gln Ser Val Gly Lys His Lys Asn Ser
1               5                   10                  15

<210> SEQ ID NO 39
<211> LENGTH: 15
<212> TYPE: PRT
<213> ORGANISM: artificial sequence
<220> FEATURE:
<223> OTHER INFORMATION: Synthetic construct

<400> SEQUENCE: 39

Asn Gly Pro Glu Val Arg Gln Ile Pro Ala Asn Phe Glu Lys Leu
1               5                   10                  15

<210> SEQ ID NO 40
<211> LENGTH: 20
<212> TYPE: PRT
<213> ORGANISM: artificial sequence
<220> FEATURE:
<223> OTHER INFORMATION: Synthetic construct

<400> SEQUENCE: 40

Asn Asn Thr Ser Ala Asp Asn Pro Pro Glu Thr Asp Ser Lys His His
1               5                   10                  15

Leu Ser Met Ser
            20

<210> SEQ ID NO 41
<211> LENGTH: 20
<212> TYPE: PRT
<213> ORGANISM: artificial sequence
<220> FEATURE:
<223> OTHER INFORMATION: Synthetic construct

<400> SEQUENCE: 41

Asn Asn Thr Trp Pro Glu Gly Ala Gly His Thr Met Pro Ser Thr Asn
1               5                   10                  15

Ile Arg Gln Ala
            20

<210> SEQ ID NO 42
<211> LENGTH: 20

```
<212> TYPE: PRT
<213> ORGANISM: artificial sequence
<220> FEATURE:
<223> OTHER INFORMATION: Synthetic construct

<400> SEQUENCE: 42

Asn Pro Thr Ala Thr Pro His Met Lys Asp Pro Met His Ser Asn Ala
1               5                   10                  15

His Ser Ser Ala
            20

<210> SEQ ID NO 43
<211> LENGTH: 20
<212> TYPE: PRT
<213> ORGANISM: artificial sequence
<220> FEATURE:
<223> OTHER INFORMATION: Synthetic construct

<400> SEQUENCE: 43

Asn Pro Thr Asp His Ile Pro Ala Asn Ser Thr Asn Ser Arg Val Ser
1               5                   10                  15

Lys Gly Asn Thr
            20

<210> SEQ ID NO 44
<211> LENGTH: 15
<212> TYPE: PRT
<213> ORGANISM: artificial sequence
<220> FEATURE:
<223> OTHER INFORMATION: Synthetic construct

<400> SEQUENCE: 44

Asn Pro Thr Asp Ser Thr His Met Met His Ala Arg Asn His Glu
1               5                   10                  15

<210> SEQ ID NO 45
<211> LENGTH: 14
<212> TYPE: PRT
<213> ORGANISM: artificial sequence
<220> FEATURE:
<223> OTHER INFORMATION: Synthetic construct

<400> SEQUENCE: 45

Gln His Cys Ile Thr Glu Arg Leu His Pro Pro Cys Thr Lys
1               5                   10

<210> SEQ ID NO 46
<211> LENGTH: 14
<212> TYPE: PRT
<213> ORGANISM: artificial sequence
<220> FEATURE:
<223> OTHER INFORMATION: Synthetic construct

<400> SEQUENCE: 46

Thr Pro Cys Ala Pro Ala Ser Phe Asn Pro His Cys Ser Arg
1               5                   10

<210> SEQ ID NO 47
<211> LENGTH: 14
<212> TYPE: PRT
<213> ORGANISM: artificial sequence
<220> FEATURE:
<223> OTHER INFORMATION: Synthetic construct

<400> SEQUENCE: 47

Thr Pro Cys Ala Thr Tyr Pro His Phe Ser Gly Cys Arg Ala
```

-continued

```
<210> SEQ ID NO 48
<211> LENGTH: 20
<212> TYPE: PRT
<213> ORGANISM: artificial sequence
<220> FEATURE:
<223> OTHER INFORMATION: Synthetic construct

<400> SEQUENCE: 48

Trp Cys Thr Asp Phe Cys Thr Arg Ser Thr Pro Thr Ser Thr Ser Arg
1               5                   10                  15

Ser Thr Thr Ser
            20

<210> SEQ ID NO 49
<211> LENGTH: 20
<212> TYPE: PRT
<213> ORGANISM: artificial sequence
<220> FEATURE:
<223> OTHER INFORMATION: Synthetic construct

<400> SEQUENCE: 49

Ala Pro Pro Leu Lys Thr Tyr Met Gln Glu Arg Glu Leu Thr Met Ser
1               5                   10                  15

Gln Asn Lys Asp
            20

<210> SEQ ID NO 50
<211> LENGTH: 20
<212> TYPE: PRT
<213> ORGANISM: artificial sequence
<220> FEATURE:
<223> OTHER INFORMATION: Synthetic construct

<400> SEQUENCE: 50

Glu Pro Pro Thr Arg Thr Arg Val Asn Asn His Thr Val Thr Val Gln
1               5                   10                  15

Ala Gln Gln His
            20

<210> SEQ ID NO 51
<211> LENGTH: 14
<212> TYPE: PRT
<213> ORGANISM: artificial sequence
<220> FEATURE:
<223> OTHER INFORMATION: Synthetic construct

<400> SEQUENCE: 51

Gly Tyr Cys Leu Arg Gly Asp Glu Pro Ala Val Cys Ser Gly
1               5                   10

<210> SEQ ID NO 52
<211> LENGTH: 20
<212> TYPE: PRT
<213> ORGANISM: artificial sequence
<220> FEATURE:
<223> OTHER INFORMATION: Synthetic construct

<400> SEQUENCE: 52

Leu Ser Ser Lys Asp Phe Gly Val Thr Asn Thr Asp Gln Arg Thr Tyr
1               5                   10                  15

Asp Tyr Thr Thr
            20
```

```
<210> SEQ ID NO 53
<211> LENGTH: 14
<212> TYPE: PRT
<213> ORGANISM: artificial sequence
<220> FEATURE:
<223> OTHER INFORMATION: Synthetic construct

<400> SEQUENCE: 53

Asn Phe Cys Glu Thr Gln Leu Asp Leu Ser Val Cys Thr Val
1               5                   10

<210> SEQ ID NO 54
<211> LENGTH: 14
<212> TYPE: PRT
<213> ORGANISM: artificial sequence
<220> FEATURE:
<223> OTHER INFORMATION: Synthetic construct

<400> SEQUENCE: 54

Asn Thr Cys Gln Pro Thr Lys Asn Ala Thr Pro Cys Ser Ala
1               5                   10

<210> SEQ ID NO 55
<211> LENGTH: 20
<212> TYPE: PRT
<213> ORGANISM: artificial sequence
<220> FEATURE:
<223> OTHER INFORMATION: Synthetic construct

<400> SEQUENCE: 55

Pro Ser Glu Pro Glu Arg Arg Asp Arg Asn Ile Ala Ala Asn Ala Gly
1               5                   10                  15

Arg Phe Asn Thr
            20

<210> SEQ ID NO 56
<211> LENGTH: 18
<212> TYPE: PRT
<213> ORGANISM: artificial sequence
<220> FEATURE:
<223> OTHER INFORMATION: Synthetic construct

<400> SEQUENCE: 56

Thr His Asn Met Ser His Phe Pro Pro Ser Gly His Pro Lys Arg Thr
1               5                   10                  15

Ala Thr

<210> SEQ ID NO 57
<211> LENGTH: 14
<212> TYPE: PRT
<213> ORGANISM: artificial sequence
<220> FEATURE:
<223> OTHER INFORMATION: Synthetic construct

<400> SEQUENCE: 57

Thr Thr Cys Pro Thr Met Gly Thr Tyr His Val Cys Trp Leu
1               5                   10

<210> SEQ ID NO 58
<211> LENGTH: 20
<212> TYPE: PRT
<213> ORGANISM: artificial sequence
<220> FEATURE:
<223> OTHER INFORMATION: Synthetic construct

<400> SEQUENCE: 58
```

```
Tyr Cys Ala Asp His Thr Pro Asp Pro Ala Asn Pro Asn Lys Ile Cys
1               5                   10                  15

Gly Tyr Ser His
            20
```

<210> SEQ ID NO 59
<211> LENGTH: 20
<212> TYPE: PRT
<213> ORGANISM: artificial sequence
<220> FEATURE:
<223> OTHER INFORMATION: Synthetic construct

<400> SEQUENCE: 59

```
Ala Ala Asn Pro His Thr Glu Trp Asp Arg Asp Ala Phe Gln Leu Ala
1               5                   10                  15

Met Pro Pro Lys
            20
```

<210> SEQ ID NO 60
<211> LENGTH: 20
<212> TYPE: PRT
<213> ORGANISM: artificial sequence
<220> FEATURE:
<223> OTHER INFORMATION: Synthetic construct

<400> SEQUENCE: 60

```
Asp Leu His Pro Met Asp Pro Ser Asn Lys Arg Pro Asp Asn Pro Ser
1               5                   10                  15

Asp Leu His Thr
            20
```

<210> SEQ ID NO 61
<211> LENGTH: 14
<212> TYPE: PRT
<213> ORGANISM: artificial sequence
<220> FEATURE:
<223> OTHER INFORMATION: Synthetic construct

<400> SEQUENCE: 61

```
Glu Ser Cys Val Ser Asn Ala Leu Met Asn Gln Cys Ile Tyr
1               5                   10
```

<210> SEQ ID NO 62
<211> LENGTH: 20
<212> TYPE: PRT
<213> ORGANISM: artificial sequence
<220> FEATURE:
<223> OTHER INFORMATION: Synthetic construct

<400> SEQUENCE: 62

```
His Asn Lys Ala Asp Ser Trp Asp Pro Asp Leu Pro Pro His Ala Gly
1               5                   10                  15

Met Ser Leu Gly
            20
```

<210> SEQ ID NO 63
<211> LENGTH: 20
<212> TYPE: PRT
<213> ORGANISM: artificial sequence
<220> FEATURE:
<223> OTHER INFORMATION: Synthetic construct

<400> SEQUENCE: 63

```
Leu Asn Asp Gln Arg Lys Pro Gly Pro Pro Thr Met Pro Thr His Ser
```

Pro Ala Val Gly
            20

<210> SEQ ID NO 64
<211> LENGTH: 14
<212> TYPE: PRT
<213> ORGANISM: artificial sequence
<220> FEATURE:
<223> OTHER INFORMATION: Synthetic construct

<400> SEQUENCE: 64

Asn Thr Cys Ala Thr Ser Pro Asn Ser Tyr Thr Cys Ser Asn
1               5                   10

<210> SEQ ID NO 65
<211> LENGTH: 14
<212> TYPE: PRT
<213> ORGANISM: artificial sequence
<220> FEATURE:
<223> OTHER INFORMATION: Synthetic construct

<400> SEQUENCE: 65

Ser Asp Cys Thr Ala Gly Leu Val Pro Pro Leu Cys Ala Thr
1               5                   10

<210> SEQ ID NO 66
<211> LENGTH: 20
<212> TYPE: PRT
<213> ORGANISM: artificial sequence
<220> FEATURE:
<223> OTHER INFORMATION: Synthetic construct

<400> SEQUENCE: 66

Thr Ile Glu Ser Ser Gln His Ser Arg Thr His Gln Gln Asn Tyr Gly
1               5                   10                  15

Ser Thr Lys Thr
            20

<210> SEQ ID NO 67
<211> LENGTH: 20
<212> TYPE: PRT
<213> ORGANISM: artificial sequence
<220> FEATURE:
<223> OTHER INFORMATION: Synthetic construct

<400> SEQUENCE: 67

Val Gly Thr Met Lys Gln His Pro Thr Thr Thr Gln Pro Pro Arg Val
1               5                   10                  15

Ser Ala Thr Asn
            20

<210> SEQ ID NO 68
<211> LENGTH: 20
<212> TYPE: PRT
<213> ORGANISM: artificial sequence
<220> FEATURE:
<223> OTHER INFORMATION: Synthetic construct

<400> SEQUENCE: 68

Tyr Ser Glu Thr Pro Asn Asp Gln Lys Pro Asn Pro His Tyr Lys Val
1               5                   10                  15

Ser Gly Thr Lys
            20

```
<210> SEQ ID NO 69
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 69

Asn Gly Asn Asn His Thr Asp Ile Pro Asn Arg Ser Ser Tyr Thr Gly
1               5                   10                  15

Gly Ser Phe Ala
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 70

Thr Met Thr Asn His Val Tyr Asn Ser Tyr Thr Glu Lys His Ser Ser
1               5                   10                  15

Thr His Arg Ser
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 71

Thr Thr Tyr His Tyr Lys Asn Ile Tyr Gln Glu Ser Tyr Gln Gln Arg
1               5                   10                  15

Asn Pro Ala Val
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 72

Val Glu Pro Ala Thr Lys Asn Met Arg Glu Ala Arg Ser Ser Thr Gln
1               5                   10                  15

Met Arg Arg Ile
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 73

Tyr Leu Leu Pro Lys Asp Gln Thr Thr Ala Pro Gln Val Thr Pro Ile
1               5                   10                  15

Val Gln His Lys
            20
```

```
<210> SEQ ID NO 74
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 74

Ala Ser Asn Leu Asp Ser Thr Phe Thr Ala Ile Asn Thr Pro Ala Cys
1               5                   10                  15

Cys Thr

<210> SEQ ID NO 75
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 75

Glu Phe Pro Tyr Tyr Asn Asp Asn Pro Pro Asn Pro Glu Arg His Thr
1               5                   10                  15

Leu Arg

<210> SEQ ID NO 76
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 76

Gly Met Pro Thr Arg Tyr Tyr His Asn Thr Pro Pro His Leu Thr Pro
1               5                   10                  15

Lys Phe

<210> SEQ ID NO 77
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 77

His Lys Asn Ala Ile Gln Pro Val Asn Asp Ala Thr Thr Leu Asp Thr
1               5                   10                  15

Thr Met

<210> SEQ ID NO 78
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 78

Ala Val Val Pro Ala Asp Leu Asn Asp His Ala Asn His Leu Ser
1               5                   10                  15

<210> SEQ ID NO 79
<211> LENGTH: 15
<212> TYPE: PRT
<213> ORGANISM: Artificial Sequence
```

```
<220> FEATURE:
<223> OTHER INFORMATION: Synthetic oral-surface binding peptide

<400> SEQUENCE: 79

Asp Leu Gly Thr Phe Pro Asn Arg Thr Leu Lys Met Ala Ala His
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 80

Phe Asp Gly Ile Gly Leu Gly Thr Ala Thr Arg His Gln Asn Arg
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 81

Gln Ala Ala Gln Val His Met Met Gln His Ser Arg Pro Thr Thr
1               5                   10                  15

<210> SEQ ID NO 82
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 82

Ser Glu Ala Arg Ala Arg Thr Phe Asn Asp His Thr Thr Pro Met Pro
1               5                   10                  15

Ile Ile

<210> SEQ ID NO 83
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 83

Glu Leu Asp His Asp Ser Arg His Tyr Met Asn Gly Leu Gln Arg Lys
1               5                   10                  15

Val Thr

<210> SEQ ID NO 84
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 84

Gly Pro Gln His Val Leu Met Gln Asp Thr His Gln Gly Tyr Ala Phe
1               5                   10                  15

Asp Asn
```

<210> SEQ ID NO 85
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 85

```
Thr Thr Gly Ser Ser Ser Gln Ala Asp Thr Ser Ala Ser Met Ser Ile
1               5                   10                  15

Val Pro Ala His
            20
```

<210> SEQ ID NO 86
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 86

```
Lys Ala Pro Ile Ala Asn Met Leu Gln Pro His Ser Tyr Gln Tyr Ser
1               5                   10                  15

Val Ala
```

<210> SEQ ID NO 87
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 87

```
Thr Tyr Gln Gly Val Pro Ser Trp Pro Ala Val Ile Asp Asp Ala Ile
1               5                   10                  15

Arg Arg
```

<210> SEQ ID NO 88
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 88

```
Val Asn Pro Asn Trp Val Glu Thr Gln Ala Leu His Gln Pro Pro Gly
1               5                   10                  15

Asn Thr
```

<210> SEQ ID NO 89
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 89

```
Asp His Asn Asn Arg Gln His Ala Val Glu Val Arg Glu Asn Lys Thr
1               5                   10                  15

His Thr Ala Arg
            20
```

<210> SEQ ID NO 90

```
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 90

Ile Tyr Pro Asn Glu Ser Met Ser Thr Ser Asn Val Arg Gly Pro Tyr
1               5                   10                  15

His Pro

<210> SEQ ID NO 91
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 91

His Asp Pro Asn His Leu Thr His Gln Ala Arg Thr Ile Tyr Arg Asn
1               5                   10                  15

Ala Asn His Thr
            20

<210> SEQ ID NO 92
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 92

Ser Asn Ala Thr Met Tyr Asn Ile Gln Ser His Ser His His Gln
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 93

Ala Asn Glu Leu Ser Thr Tyr Ala Gln Thr Asn Pro Gly Ser Gly
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 94

Asp Thr Ile His Pro Asn Lys Met Lys Ser Pro Ser Ser Pro Leu
1               5                   10                  15

<210> SEQ ID NO 95
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 95

Ala Pro Pro Thr Tyr Gln Thr Ala Ser Tyr Pro His Asn Leu Pro Ser
```

```
1               5                   10                  15
Lys Arg Lys Met
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 96

Gln Val Pro Asp Tyr Leu Ser Pro Thr His Gln Lys Lys Ala Phe Leu
1               5                   10                  15

Glu Ile Pro Thr
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 97

Thr Asn Asp Leu His Ala Asn Pro Phe Thr Gly Thr Tyr Ile Ala Pro
1               5                   10                  15

Asp Pro Thr Ser
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 98

His Lys Asn Glu Asn Ile Met Gln Tyr Asn Val Asn Asp Arg Trp His
1               5                   10                  15

Ile Thr Pro Ala
            20

<210> SEQ ID NO 99
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 99

Ile Asp Gly Pro His His Ser Pro Val His Arg Tyr His Thr Pro Ser
1               5                   10                  15

Ile Thr

<210> SEQ ID NO 100
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 100

Ala Ile Glu Tyr Gln His Ser Ala Thr Thr Pro Trp Thr Met Arg Thr
```

```
1               5                   10                  15
Arg Leu Pro Pro
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 101

Glu Phe Tyr Pro Phe Ala Glu Val Pro Pro Glu Lys Ser Gly Ile Gly
1               5                   10                  15

Arg Gln Val Phe
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 102

Gly Val His Gln Tyr Ser Arg Pro Thr Val Pro Ser Tyr Leu Trp Thr
1               5                   10                  15

Ser Gly Gln His
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 103

Gly Tyr Gln Pro His Tyr Val Asp His Thr Ile Gly Trp Gln Pro Met
1               5                   10                  15

Ile Arg Pro Asn
            20

<210> SEQ ID NO 104
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 104

Gln Phe Asn Gln Thr Ser His Ser Phe Met His Gly Thr Ser Gly Tyr
1               5                   10                  15

Val Pro Gly Lys
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 105
```

```
Ser Phe Ser Trp His Arg Gly Asp Trp Glu Leu Gly His Gln Ser Lys
1               5                   10                  15

Thr Met Gly Met
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 106

Ser Met Trp His Asp Ile Thr Lys Arg Tyr Arg Asn Pro Ser Glu Met
1               5                   10                  15

Val Ser Ala Tyr
            20

<210> SEQ ID NO 107
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 107

Thr His Gly Asn Lys His Gln Ser Trp Thr Tyr Pro Ser Glu Ile Asn
1               5                   10                  15

His Lys Asn Tyr
            20

<210> SEQ ID NO 108
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 108

Trp His Glu Pro His Gln Phe Ser Gly Glu Asn Thr Asp Tyr Ser Ser
1               5                   10                  15

Ser Met Gly Thr
            20

<210> SEQ ID NO 109
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 109

Thr His Gly Asn Lys His Gln Ser Trp Thr Tyr Pro Ser Glu Ile Asn
1               5                   10                  15

His Lys Asn Tyr
            20

<210> SEQ ID NO 110
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 110
```

```
Asp Gly Tyr Lys Leu Gln Thr Ser Leu Asp Trp Gln Met Trp Asn Pro
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 111

Phe Pro Ser Lys Trp Tyr Asn His His Arg His Ile Thr Gly His Val
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 112

Gly Gly Met Gly Ala Leu Glu Ser Tyr Arg Gln Trp Asn His Leu Ala
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 113

Gly Ile Asn Lys Gly Gln Arg Pro Pro Trp Glu Ser Trp His Glu Asn
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 114

Gly Tyr Gly Gln Tyr Val Ser Gln Gln Thr Trp Ala His Ser Asn Lys
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 115

His Asp His Leu Ser Trp Trp Gly Gln Phe Asp Arg Gln Asn Leu Leu
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 116
```

```
Met Pro Gly His Gln Glu Ser Ile Lys Val Gln Asn Trp Asn Arg Val
1               5                   10                  15
```

<210> SEQ ID NO 117
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 117

```
Asn Leu His Ser Pro Trp Pro Ser His Ala Ala His His Trp Ser Thr
1               5                   10                  15
```

<210> SEQ ID NO 118
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 118

```
Asn Gln Gln Met Lys Leu Val Pro Gln His Trp His Arg Ala Gln Pro
1               5                   10                  15
```

<210> SEQ ID NO 119
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 119

```
Ser Glu Lys Trp Phe Asn Pro Gly Pro Trp Pro Lys Leu Ala Thr Gln
1               5                   10                  15
```

<210> SEQ ID NO 120
<211> LENGTH: 25
<212> TYPE: PRT
<213> ORGANISM: Artificial Sequence
<220> FEATURE:
<223> OTHER INFORMATION: synthetic construct

<400> SEQUENCE: 120

```
Ser Ser Arg Pro Asn Gly Asn Asn His Thr Asp Ile Pro Asn Arg Ser
1               5                   10                  15

Ser Tyr Thr Gly Gly Ser Phe Ala Lys
            20                  25
```

<210> SEQ ID NO 121
<211> LENGTH: 25
<212> TYPE: PRT
<213> ORGANISM: Artificial Sequence
<220> FEATURE:
<223> OTHER INFORMATION: synthetic construct

<400> SEQUENCE: 121

```
Ser Ser Arg Pro Thr Met Thr Asn His Val Tyr Asn Ser Tyr Thr Glu
1               5                   10                  15

Lys His Ser Ser Thr His Arg Ser Lys
            20                  25
```

<210> SEQ ID NO 122
<211> LENGTH: 25
<212> TYPE: PRT
<213> ORGANISM: Artificial Sequence
<220> FEATURE:
<223> OTHER INFORMATION: synthetic construct

<400> SEQUENCE: 122

Ser Ser Arg Pro Thr Thr Tyr His Tyr Lys Asn Ile Tyr Gln Glu Ser
1               5                   10                  15

Tyr Gln Gln Arg Asn Pro Ala Val Lys
            20                  25

<210> SEQ ID NO 123
<211> LENGTH: 25
<212> TYPE: PRT
<213> ORGANISM: Artificial Sequence
<220> FEATURE:
<223> OTHER INFORMATION: synthetic construct

<400> SEQUENCE: 123

Ser Ser Arg Pro Val Glu Pro Ala Thr Lys Asn Met Arg Glu Ala Arg
1               5                   10                  15

Ser Ser Thr Gln Met Arg Arg Ile Lys
            20                  25

<210> SEQ ID NO 124
<211> LENGTH: 25
<212> TYPE: PRT
<213> ORGANISM: Artificial Sequence
<220> FEATURE:
<223> OTHER INFORMATION: synthetic construct

<400> SEQUENCE: 124

Ser Ser Arg Pro Tyr Leu Leu Pro Lys Asp Gln Thr Thr Ala Pro Gln
1               5                   10                  15

Val Thr Pro Ile Val Gln His Lys Lys
            20                  25

<210> SEQ ID NO 125
<211> LENGTH: 23
<212> TYPE: PRT
<213> ORGANISM: Artificial Sequence
<220> FEATURE:
<223> OTHER INFORMATION: synthetic construct

<400> SEQUENCE: 125

Ser Ser Arg Pro Glu Phe Pro Tyr Tyr Asn Asp Asn Pro Pro Asn Pro
1               5                   10                  15

Glu Arg His Thr Leu Arg Lys
            20

<210> SEQ ID NO 126
<211> LENGTH: 20
<212> TYPE: PRT
<213> ORGANISM: Artificial Sequence
<220> FEATURE:
<223> OTHER INFORMATION: synthetic construct

<400> SEQUENCE: 126

Ser Ser Arg Pro Asp Leu Gly Thr Phe Pro Asn Arg Thr Leu Lys Met
1               5                   10                  15

Ala Ala His Lys
            20

<210> SEQ ID NO 127
<211> LENGTH: 20
<212> TYPE: PRT

<213> ORGANISM: Artificial Sequence
<220> FEATURE:
<223> OTHER INFORMATION: synthetic construct

<400> SEQUENCE: 127

Ser Ser Arg Pro Phe Asp Gly Ile Gly Leu Gly Thr Ala Thr Arg His
1               5                   10                  15

Gln Asn Arg Lys
            20

<210> SEQ ID NO 128
<211> LENGTH: 20
<212> TYPE: PRT
<213> ORGANISM: Artificial Sequence
<220> FEATURE:
<223> OTHER INFORMATION: synthetic construct

<400> SEQUENCE: 128

Ser Ser Arg Pro Gln Ala Ala Gln Val His Met Met Gln His Ser Arg
1               5                   10                  15

Pro Thr Thr Lys
            20

<210> SEQ ID NO 129
<211> LENGTH: 23
<212> TYPE: PRT
<213> ORGANISM: Artificial Sequence
<220> FEATURE:
<223> OTHER INFORMATION: synthetic construct

<400> SEQUENCE: 129

Ser Ser Arg Pro Ser Glu Ala Arg Ala Arg Thr Phe Asn Asp His Thr
1               5                   10                  15

Thr Pro Met Pro Ile Ile Lys
            20

<210> SEQ ID NO 130
<211> LENGTH: 23
<212> TYPE: PRT
<213> ORGANISM: Artificial Sequence
<220> FEATURE:
<223> OTHER INFORMATION: synthetic construct

<400> SEQUENCE: 130

Ser Ser Arg Pro Glu Leu Asp His Asp Ser Arg His Tyr Met Asn Gly
1               5                   10                  15

Leu Gln Arg Lys Val Thr Lys
            20

<210> SEQ ID NO 131
<211> LENGTH: 23
<212> TYPE: PRT
<213> ORGANISM: Artificial Sequence
<220> FEATURE:
<223> OTHER INFORMATION: synthetic construct

<400> SEQUENCE: 131

Ser Ser Arg Pro Gly Pro Gln His Val Leu Met Gln Asp Thr His Gln
1               5                   10                  15

Gly Tyr Ala Phe Asp Asn Lys
            20

<210> SEQ ID NO 132
<211> LENGTH: 25

```
<212> TYPE: PRT
<213> ORGANISM: Artificial Sequence
<220> FEATURE:
<223> OTHER INFORMATION: synthetic construct

<400> SEQUENCE: 132

Ser Ser Arg Pro Thr Thr Gly Ser Ser Gln Ala Asp Thr Ser Ala
1               5                   10                  15

Ser Met Ser Ile Val Pro Ala His Lys
            20                  25

<210> SEQ ID NO 133
<211> LENGTH: 23
<212> TYPE: PRT
<213> ORGANISM: Artificial Sequence
<220> FEATURE:
<223> OTHER INFORMATION: synthetic construct

<400> SEQUENCE: 133

Ser Ser Arg Pro Thr Tyr Gln Gly Val Pro Ser Trp Pro Ala Val Ile
1               5                   10                  15

Asp Asp Ala Ile Arg Arg Lys
            20

<210> SEQ ID NO 134
<211> LENGTH: 23
<212> TYPE: PRT
<213> ORGANISM: Artificial Sequence
<220> FEATURE:
<223> OTHER INFORMATION: synthetic construct

<400> SEQUENCE: 134

Ser Ser Arg Pro Val Asn Pro Asn Trp Val Glu Thr Gln Ala Leu His
1               5                   10                  15

Gln Pro Pro Gly Asn Thr Lys
            20

<210> SEQ ID NO 135
<211> LENGTH: 23
<212> TYPE: PRT
<213> ORGANISM: Artificial Sequence
<220> FEATURE:
<223> OTHER INFORMATION: synthetic construct

<400> SEQUENCE: 135

Ser Ser Arg Pro Ile Tyr Pro Asn Glu Ser Met Ser Thr Ser Asn Val
1               5                   10                  15

Arg Gly Pro Tyr His Pro Lys
            20

<210> SEQ ID NO 136
<211> LENGTH: 25
<212> TYPE: PRT
<213> ORGANISM: Artificial Sequence
<220> FEATURE:
<223> OTHER INFORMATION: synthetic construct

<400> SEQUENCE: 136

Ser Ser Arg Pro His Asp Pro Asn His Leu Thr His Gln Ala Arg Thr
1               5                   10                  15

Ile Tyr Arg Asn Ala Asn His Thr Lys
            20                  25

<210> SEQ ID NO 137
```

<211> LENGTH: 25
<212> TYPE: PRT
<213> ORGANISM: Artificial Sequence
<220> FEATURE:
<223> OTHER INFORMATION: synthetic construct

<400> SEQUENCE: 137

Ser Ser Arg Pro Ala Pro Pro Thr Tyr Gln Thr Ala Ser Tyr Pro His
1               5                   10                  15

Asn Leu Pro Ser Lys Arg Lys Met Lys
            20                  25

<210> SEQ ID NO 138
<211> LENGTH: 25
<212> TYPE: PRT
<213> ORGANISM: Artificial Sequence
<220> FEATURE:
<223> OTHER INFORMATION: synthetic construct

<400> SEQUENCE: 138

Ser Ser Arg Pro Gln Val Pro Asp Tyr Leu Ser Pro Thr His Gln Lys
1               5                   10                  15

Lys Ala Phe Leu Glu Ile Pro Thr Lys
            20                  25

<210> SEQ ID NO 139
<211> LENGTH: 25
<212> TYPE: PRT
<213> ORGANISM: Artificial Sequence
<220> FEATURE:
<223> OTHER INFORMATION: synthetic construct

<400> SEQUENCE: 139

Ser Ser Arg Pro His Lys Asn Glu Asn Ile Met Gln Tyr Asn Val Asn
1               5                   10                  15

Asp Arg Trp His Ile Thr Pro Ala Lys
            20                  25

<210> SEQ ID NO 140
<211> LENGTH: 15
<212> TYPE: PRT
<213> ORGANISM: artificial sequence
<220> FEATURE:
<223> OTHER INFORMATION: synthetic construct

<400> SEQUENCE: 140

Ser Asn Ala Thr Met Tyr Asn Ile Gln Ser His Ser His His Gln
1               5                   10                  15

<210> SEQ ID NO 141
<211> LENGTH: 15
<212> TYPE: PRT
<213> ORGANISM: artificial sequence
<220> FEATURE:
<223> OTHER INFORMATION: synthetic construct

<400> SEQUENCE: 141

Gln Ala Ala Gln Val His Met Met Gln His Ser Arg Pro Thr Thr
1               5                   10                  15

<210> SEQ ID NO 142
<211> LENGTH: 15
<212> TYPE: PRT
<213> ORGANISM: artificial sequence
<220> FEATURE:
<223> OTHER INFORMATION: synthetic construct

<400> SEQUENCE: 142

His Asp Pro Tyr Thr Met Lys Ser Ala Leu Arg Gln Ser Thr Ser
1               5                   10                  15

<210> SEQ ID NO 143
<211> LENGTH: 15
<212> TYPE: PRT
<213> ORGANISM: artificial sequence
<220> FEATURE:
<223> OTHER INFORMATION: synthetic construct

<400> SEQUENCE: 143

Asp Leu Gly Thr Phe Pro Asn Arg Thr Leu Lys Met Ala Ala His
1               5                   10                  15

<210> SEQ ID NO 144
<211> LENGTH: 15
<212> TYPE: PRT
<213> ORGANISM: artificial sequence
<220> FEATURE:
<223> OTHER INFORMATION: synthetic construct

<400> SEQUENCE: 144

Asp Thr Ile His Pro Asn Lys Met Lys Ser Pro Ser Ser Pro Leu
1               5                   10                  15

<210> SEQ ID NO 145
<211> LENGTH: 15
<212> TYPE: PRT
<213> ORGANISM: artificial sequence
<220> FEATURE:
<223> OTHER INFORMATION: synthetic construct

<400> SEQUENCE: 145

Gly Ser Asn Asn His Leu Pro Ser Thr Val Pro Arg Leu Thr Val
1               5                   10                  15

<210> SEQ ID NO 146
<211> LENGTH: 18
<212> TYPE: PRT
<213> ORGANISM: artificial sequence
<220> FEATURE:
<223> OTHER INFORMATION: synthetic construct

<400> SEQUENCE: 146

Ser Asn Pro Ile Pro Asn Phe Ala His Asp Leu Arg His Ser Lys Tyr
1               5                   10                  15

Asn Ser

<210> SEQ ID NO 147
<211> LENGTH: 18
<212> TYPE: PRT
<213> ORGANISM: artificial sequence
<220> FEATURE:
<223> OTHER INFORMATION: synthetic construct

<400> SEQUENCE: 147

Thr Lys Pro Pro Arg Thr Pro Thr Ala Asn Thr Ser Arg Pro His His
1               5                   10                  15

Asn Phe

<210> SEQ ID NO 148
<211> LENGTH: 20
<212> TYPE: PRT

```
<213> ORGANISM: artificial sequence
<220> FEATURE:
<223> OTHER INFORMATION: synthetic construct

<400> SEQUENCE: 148

Ala Asn Ser Gly Phe Pro Ile Trp Leu Gln Lys Tyr Pro Trp Ser Glu
1               5                   10                  15

Val Gln Gln Glu
            20

<210> SEQ ID NO 149
<211> LENGTH: 19
<212> TYPE: PRT
<213> ORGANISM: artificial sequence
<220> FEATURE:
<223> OTHER INFORMATION: synthetic construct

<400> SEQUENCE: 149

Ala Thr Pro Arg Leu Thr Pro Glu Ala His His Lys Ala Gly Asn Trp
1               5                   10                  15

Tyr Ala Ser

<210> SEQ ID NO 150
<211> LENGTH: 20
<212> TYPE: PRT
<213> ORGANISM: artificial sequence
<220> FEATURE:
<223> OTHER INFORMATION: synthetic construct

<400> SEQUENCE: 150

Ala Thr Pro Ser Gln His Arg Tyr Gly Leu Met Gln Asn His Ala Pro
1               5                   10                  15

Asn Gly Ile Glu
            20

<210> SEQ ID NO 151
<211> LENGTH: 16
<212> TYPE: PRT
<213> ORGANISM: artificial sequence
<220> FEATURE:
<223> OTHER INFORMATION: synthetic construct

<400> SEQUENCE: 151

Gly Met Gly Ser Glu Val Leu Ser Gln Tyr Pro Gln Ala Pro Val Gly
1               5                   10                  15

<210> SEQ ID NO 152
<211> LENGTH: 21
<212> TYPE: PRT
<213> ORGANISM: artificial sequence
<220> FEATURE:
<223> OTHER INFORMATION: synthetic construct

<400> SEQUENCE: 152

Thr Thr Tyr His Tyr Lys Asn Ile Tyr Gln Glu Ser Tyr Gln Gln Arg
1               5                   10                  15

Asn Pro Ala Val Lys
            20

<210> SEQ ID NO 153
<211> LENGTH: 16
<212> TYPE: PRT
<213> ORGANISM: artificial sequence
<220> FEATURE:
<223> OTHER INFORMATION: synthetic construct
```

<400> SEQUENCE: 153

Ser Asn Ala Thr Met Tyr Asn Ile Gln Ser His Ser His His Gln Lys
1               5                   10                  15

<210> SEQ ID NO 154
<211> LENGTH: 16
<212> TYPE: PRT
<213> ORGANISM: artificial sequence
<220> FEATURE:
<223> OTHER INFORMATION: synthetic construct

<400> SEQUENCE: 154

Gln Ala Ala Gln Val His Met Met Gln His Ser Arg Pro Thr Thr Lys
1               5                   10                  15

<210> SEQ ID NO 155
<211> LENGTH: 16
<212> TYPE: PRT
<213> ORGANISM: artificial sequence
<220> FEATURE:
<223> OTHER INFORMATION: synthetic construct

<400> SEQUENCE: 155

His Asp Pro Tyr Thr Met Lys Ser Ala Leu Arg Gln Ser Thr Ser Lys
1               5                   10                  15

<210> SEQ ID NO 156
<211> LENGTH: 16
<212> TYPE: PRT
<213> ORGANISM: artificial sequence
<220> FEATURE:
<223> OTHER INFORMATION: synthetic construct

<400> SEQUENCE: 156

Asp Leu Gly Thr Phe Pro Asn Arg Thr Leu Lys Met Ala Ala His Lys
1               5                   10                  15

<210> SEQ ID NO 157
<211> LENGTH: 16
<212> TYPE: PRT
<213> ORGANISM: artificial sequence
<220> FEATURE:
<223> OTHER INFORMATION: synthetic construct

<400> SEQUENCE: 157

Asp Thr Ile His Pro Asn Lys Met Lys Ser Pro Ser Ser Pro Leu Lys
1               5                   10                  15

<210> SEQ ID NO 158
<211> LENGTH: 16
<212> TYPE: PRT
<213> ORGANISM: artificial sequence
<220> FEATURE:
<223> OTHER INFORMATION: synthetic construct

<400> SEQUENCE: 158

Gly Ser Asn Asn His Leu Pro Ser Thr Val Pro Arg Leu Thr Val Lys
1               5                   10                  15

<210> SEQ ID NO 159
<211> LENGTH: 19
<212> TYPE: PRT
<213> ORGANISM: artificial sequence
<220> FEATURE:
<223> OTHER INFORMATION: synthetic construct

```
<400> SEQUENCE: 159

Ser Asn Pro Ile Pro Asn Phe Ala His Asp Leu Arg His Ser Lys Tyr
1               5                   10                  15

Asn Ser Lys

<210> SEQ ID NO 160
<211> LENGTH: 19
<212> TYPE: PRT
<213> ORGANISM: artificial sequence
<220> FEATURE:
<223> OTHER INFORMATION: synthetic construct

<400> SEQUENCE: 160

Thr Lys Pro Pro Arg Thr Pro Thr Ala Asn Thr Ser Arg Pro His His
1               5                   10                  15

Asn Phe Lys

<210> SEQ ID NO 161
<211> LENGTH: 21
<212> TYPE: PRT
<213> ORGANISM: artificial sequence
<220> FEATURE:
<223> OTHER INFORMATION: synthetic construct

<400> SEQUENCE: 161

Ala Asn Ser Gly Phe Pro Ile Trp Leu Gln Lys Tyr Pro Trp Ser Glu
1               5                   10                  15

Val Gln Gln Glu Lys
            20

<210> SEQ ID NO 162
<211> LENGTH: 21
<212> TYPE: PRT
<213> ORGANISM: artificial sequence
<220> FEATURE:
<223> OTHER INFORMATION: synthetic construct

<400> SEQUENCE: 162

Ala Thr Pro Ser Gln His Arg Tyr Gly Leu Met Gln Asn His Ala Pro
1               5                   10                  15

Asn Gly Ile Glu Lys
            20

<210> SEQ ID NO 163
<211> LENGTH: 17
<212> TYPE: PRT
<213> ORGANISM: artificial sequence
<220> FEATURE:
<223> OTHER INFORMATION: synthetic construct

<400> SEQUENCE: 163

Gly Met Gly Ser Glu Val Leu Ser Gln Tyr Pro Gln Ala Pro Val Gly
1               5                   10                  15

Lys

<210> SEQ ID NO 164
<211> LENGTH: 8
<212> TYPE: PRT
<213> ORGANISM: Artificial Sequence
<220> FEATURE:
<223> OTHER INFORMATION: Synthetic construct - caspace 3 cleavable
      linker

<400> SEQUENCE: 164
```

Leu Glu Ser Gly Asp Glu Val Asp
1               5

<210> SEQ ID NO 165
<211> LENGTH: 37
<212> TYPE: PRT
<213> ORGANISM: Artificial Sequence
<220> FEATURE:
<223> OTHER INFORMATION: synthetic construct

<400> SEQUENCE: 165

Thr Ser Thr Ser Lys Ala Ser Thr Thr Thr Thr Ser Ser Lys Thr Thr
1               5                   10                  15

Thr Thr Ser Ser Lys Thr Thr Thr Thr Thr Ser Lys Thr Ser Thr Thr
            20                  25                  30

Ser Ser Ser Ser Thr
35

<210> SEQ ID NO 166
<211> LENGTH: 22
<212> TYPE: PRT
<213> ORGANISM: Artificial Sequence
<220> FEATURE:
<223> OTHER INFORMATION: synthetic construct

<400> SEQUENCE: 166

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 167
<211> LENGTH: 10
<212> TYPE: PRT
<213> ORGANISM: Artificial Sequence
<220> FEATURE:
<223> OTHER INFORMATION: synthetic construct

<400> SEQUENCE: 167

Gly Pro Gly Gly Tyr Gly Pro Gly Gln Gln
1               5                   10

<210> SEQ ID NO 168
<211> LENGTH: 9
<212> TYPE: PRT
<213> ORGANISM: Artificial Sequence
<220> FEATURE:
<223> OTHER INFORMATION: synthetic construct

<400> SEQUENCE: 168

Gly Gly Ser Gly Pro Gly Ser Gly Gly
1               5

<210> SEQ ID NO 169
<211> LENGTH: 5
<212> TYPE: PRT
<213> ORGANISM: Artificial Sequence
<220> FEATURE:
<223> OTHER INFORMATION: synthetic construct

<400> SEQUENCE: 169

Gly Gly Pro Lys Lys
1               5

```
<210> SEQ ID NO 170
<211> LENGTH: 5
<212> TYPE: PRT
<213> ORGANISM: Artificial Sequence
<220> FEATURE:
<223> OTHER INFORMATION: synthetic construct

<400> SEQUENCE: 170

Gly Pro Gly Val Gly
1               5

<210> SEQ ID NO 171
<211> LENGTH: 7
<212> TYPE: PRT
<213> ORGANISM: Artificial Sequence
<220> FEATURE:
<223> OTHER INFORMATION: synthetic construct

<400> SEQUENCE: 171

Gly Gly Gly Cys Gly Gly Gly
1               5

<210> SEQ ID NO 172
<211> LENGTH: 4
<212> TYPE: PRT
<213> ORGANISM: Artificial Sequence
<220> FEATURE:
<223> OTHER INFORMATION: synthetic construct

<400> SEQUENCE: 172

Gly Gly Gly Cys
1

<210> SEQ ID NO 173
<211> LENGTH: 14
<212> TYPE: PRT
<213> ORGANISM: Artificial Sequence
<220> FEATURE:
<223> OTHER INFORMATION: synthetic construct

<400> SEQUENCE: 173

Pro His Met Ala Ser Met Thr Gly Gly Gln Gln Met Gly Ser
1               5                   10

<210> SEQ ID NO 174
<211> LENGTH: 16
<212> TYPE: PRT
<213> ORGANISM: Artificial Sequence
<220> FEATURE:
<223> OTHER INFORMATION: synthetic construct

<400> SEQUENCE: 174

Gly Pro Glu Glu Ala Ala Lys Lys Glu Glu Ala Ala Lys Lys Pro Ala
1               5                   10                  15

<210> SEQ ID NO 175
<211> LENGTH: 14
<212> TYPE: PRT
<213> ORGANISM: Artificial Sequence
<220> FEATURE:
<223> OTHER INFORMATION: synthetic construct

<400> SEQUENCE: 175

Gly Ser Gly Gly Gly Gly Ser Gly Ser Gly Gly Gly Gly Ser
1               5                   10

<210> SEQ ID NO 176
```

```
<211> LENGTH: 37
<212> TYPE: PRT
<213> ORGANISM: Artificial Sequence
<220> FEATURE:
<223> OTHER INFORMATION: synthetic construct

<400> SEQUENCE: 176

Gly Pro Glu Pro Glu Pro Glu Pro Ile Pro Glu Pro Pro Lys
1               5                   10                  15

Glu Ala Pro Val Val Ile Glu Lys Pro Lys Pro Lys Pro Lys
                20                  25                  30

Pro Lys Pro Pro Ala
35

<210> SEQ ID NO 177
<211> LENGTH: 18
<212> TYPE: PRT
<213> ORGANISM: artificial sequence
<220> FEATURE:
<223> OTHER INFORMATION: synthetic construct

<400> SEQUENCE: 177

Gly Pro Gly Ser Gly Gly Ala Gly Ser Pro Gly Ser Ala Gly Gly Pro
1               5                   10                  15

Gly Ser

<210> SEQ ID NO 178
<211> LENGTH: 431
<212> TYPE: PRT
<213> ORGANISM: artificial sequence
<220> FEATURE:
<223> OTHER INFORMATION: synthetic construct

<400> SEQUENCE: 178

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
```

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
            325                 330                 335

Ser Ala Gly Gly Pro Gly Ser Pro Ser Ala Gln Ser Gln Leu Pro Asp
            340                 345                 350

Lys His Ser Gly Leu His Glu Arg Ala Pro Gln Arg Tyr Gly Pro Glu
            355                 360                 365

Pro Glu Pro Glu Pro Glu Pro Ile Pro Glu Pro Pro Lys Glu Ala Pro
370                 375                 380

Val Val Ile Glu Lys Pro Lys Pro Lys Pro Lys Pro Lys Pro Lys Pro
385                 390                 395                 400

Pro Ala His Asp His Lys Asn Gln Lys Glu Thr His Gln Arg His Ala
            405                 410                 415

Ala Gly Ser Gly Gly Gly Ser Pro His His His His His
            420                 425                 430

<210> SEQ ID NO 179
<211> LENGTH: 353
<212> TYPE: PRT
<213> ORGANISM: artificial sequence
<220> FEATURE:
<223> OTHER INFORMATION: synthetic construct

<400> SEQUENCE: 179

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe

```
                130               135                 140
Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly
            180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Gly Lys Gly Lys Gly Lys Gly Lys Gly
                340                 345                 350

Lys
```

<210> SEQ ID NO 180
<211> LENGTH: 359
<212> TYPE: PRT
<213> ORGANISM: artificial sequence
<220> FEATURE:
<223> OTHER INFORMATION: synthetic construct

<400> SEQUENCE: 180

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
                50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Trp Pro Ser Met Gly Tyr Ile Cys
                100                 105                 110

Phe Val Met Asp Thr Arg Gly Gln Gly Ser Gly Trp Leu Lys Gly Asp
                115                 120                 125

Thr Pro Asp Tyr Pro Glu Gly Pro Val Asp Pro Gln Tyr Pro Gly Phe
                130                 135                 140
```

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gly Gly Gly Gly
            180                 185                 190

Ile Ala Leu Ala Val Ser Ala Leu Ser Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
290                 295                 300

Gly Gly Gly Ser Phe Gln Ala Val Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Gly Lys Gly Lys Gly Lys Gly Lys Gly
                340                 345                 350

Lys His His His His His His
                355

<210> SEQ ID NO 181
<211> LENGTH: 375
<212> TYPE: PRT
<213> ORGANISM: artificial sequence
<220> FEATURE:
<223> OTHER INFORMATION: synthetic construct

<400> SEQUENCE: 181

Met Ala Phe Phe Asp Leu Pro Leu Glu Glu Lys Lys Tyr Arg Pro
1               5                   10                  15

Glu Arg Tyr Glu Glu Lys Asp Phe Asp Glu Phe Trp Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Ala Tyr Asp Val Thr Phe Ser Gly Tyr
                50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Trp Pro Ser Met Gly Tyr Ile Cys
                100                 105                 110

Phe Val Met Asp Thr Arg Gly Gln Gly Ser Gly Trp Leu Lys Gly Asp
                115                 120                 125

Thr Pro Asp Tyr Pro Glu Gly Pro Val Asp Pro Gln Tyr Pro Gly Phe
                130                 135                 140

```
Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gly Gly Gly Gly
            180                 185                 190

Ile Ala Leu Ala Val Ser Ala Leu Ser Lys Ala Lys Ala Leu Leu
                195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Thr Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
290                 295                 300

Gly Gly Gly Ser Phe Gln Ala Val Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Thr Lys Pro Pro Arg Thr Pro Thr Ala
                340                 345                 350

Asn Thr Ser Arg Pro His His Asn Phe Gly Ser Gly Gly Gly Gly Ser
                355                 360                 365

Pro His His His His His His
    370                 375

<210> SEQ ID NO 182
<211> LENGTH: 431
<212> TYPE: PRT
<213> ORGANISM: artificial sequence
<220> FEATURE:
<223> OTHER INFORMATION: synthetic construct

<400> SEQUENCE: 182

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
            50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
                115                 120                 125
```

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Thr Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Pro Ser Ala Gln Ser Gln Leu Pro Asp
            340                 345                 350

Lys His Ser Gly Leu His Glu Arg Ala Pro Gln Arg Tyr Gly Pro Glu
        355                 360                 365

Pro Glu Pro Glu Pro Glu Pro Ile Pro Glu Pro Pro Lys Glu Ala Pro
        370                 375                 380

Val Val Ile Glu Lys Pro Lys Pro Lys Pro Lys Pro Lys Pro
385                 390                 395                 400

Pro Ala His Asp His Lys Asn Gln Lys Glu Thr His Gln Arg His Ala
                405                 410                 415

Ala Gly Ser Gly Gly Gly Gly Ser Pro His His His His His
            420                 425                 430

<210> SEQ ID NO 183
<211> LENGTH: 359
<212> TYPE: PRT
<213> ORGANISM: artificial sequence
<220> FEATURE:
<223> OTHER INFORMATION: synthetic construct

<400> SEQUENCE: 183

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Gly Lys Gly Lys Gly Lys Gly Lys Gly
            340                 345                 350

Lys His His His His His His
        355

<210> SEQ ID NO 184
<211> LENGTH: 386
<212> TYPE: PRT
<213> ORGANISM: artificial sequence
<220> FEATURE:
<223> OTHER INFORMATION: synthetic construct

<400> SEQUENCE: 184

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
            85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Pro Glu Pro Glu Gly Pro Ser Gly Gly
            325                 330                 335

Ala Gly Ser Pro Gly Ser Ala Gly Gly Pro Gly Ser Glu Pro Glu Pro
            340                 345                 350

Glu Trp Lys Thr Lys Lys Ile Leu Leu Ser Arg Thr Arg Arg Ile Met
            355                 360                 365

Arg Gln Val Val Arg Ser Val Met His Lys Ile Trp His His His His
            370                 375                 380

His His
385

<210> SEQ ID NO 185
<211> LENGTH: 387
<212> TYPE: PRT
<213> ORGANISM: artificial sequence
<220> FEATURE:
<223> OTHER INFORMATION: synthetic construct

<400> SEQUENCE: 185

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

```
Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
            130                 135                 140

Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Gly Pro Gly Ser Gly Gly Ala Gly Ser Pro Gly Ser Ala Gly Gly Pro
            340                 345                 350

Gly Ser Trp Lys Thr Lys Lys Ile Leu Leu Ser Arg Thr Arg Arg Ile
            355                 360                 365

Met Arg Gln Val Val Arg Ser Val Met His Lys Ile Trp His His His
            370                 375                 380

His His His
385

<210> SEQ ID NO 186
<211> LENGTH: 386
<212> TYPE: PRT
<213> ORGANISM: artificial sequence
<220> FEATURE:
<223> OTHER INFORMATION: synthetic construct

<400> SEQUENCE: 186
```

```
Met Ala Phe Phe Asp Leu Pro Leu Glu Glu Leu Lys Lys Tyr Arg Pro
1               5                   10                  15
Glu Arg Tyr Glu Glu Lys Asp Phe Asp Glu Phe Trp Glu Glu Thr Leu
            20                  25                  30
Ala Glu Ser Glu Lys Phe Pro Leu Asp Pro Val Phe Glu Arg Met Glu
        35                  40                  45
Ser His Leu Lys Thr Val Glu Ala Tyr Asp Val Thr Phe Ser Gly Tyr
    50                  55                  60
Arg Gly Gln Arg Ile Lys Gly Trp Leu Leu Val Pro Lys Leu Glu Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Leu Lys Gly Asp
        115                 120                 125
Thr Pro Asp Tyr Pro Glu Gly Pro Val Asp Pro Gln Tyr Pro Gly Phe
    130                 135                 140
Met Thr Arg Gly Ile Leu Asp Pro Arg Thr Tyr Tyr Arg Arg Val
145                 150                 155                 160
Phe Thr Asp Ala Val Arg Ala Val Glu Ala Ala Ser Phe Pro Gln
                165                 170                 175
Val Asp Gln Glu Arg Ile Val Ile Ala Gly Gly Ser Gln Gly Gly Gly
            180                 185                 190
Ile Ala Leu Ala Val Ser Ala Leu Ser Lys Lys Ala Lys Ala Leu Leu
        195                 200                 205
Cys Asp Val Pro Phe Leu Cys His Phe Arg Arg Ala Val Gln Leu Val
    210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
Asn Phe Ala Ala Arg Ala Lys Ile Pro Ala Leu Phe Ser Val Gly Leu
            260                 265                 270
Met Asp Asn Ile Ser Pro Pro Ser Thr Val Phe Ala Ala Tyr Asn Tyr
        275                 280                 285
Tyr Ala Gly Pro Lys Glu Ile Arg Ile Tyr Pro Tyr Asn Asn His Glu
    290                 295                 300
Gly Gly Gly Ser Phe Gln Ala Val Glu Gln Val Lys Phe Leu Lys Lys
305                 310                 315                 320
Leu Phe Glu Lys Gly Glu Pro Glu Pro Glu Gly Pro Gly Ser Gly Gly
                325                 330                 335
Ala Gly Ser Pro Gly Ser Ala Gly Gly Pro Gly Ser Glu Pro Glu Pro
            340                 345                 350
Glu Pro Leu Trp Arg Arg Ile Thr Lys Arg Lys Leu Val Arg Pro Val
        355                 360                 365
Ala Thr Leu Met Trp Tyr Trp Phe Thr Ser Lys Arg His His His His
    370                 375                 380
His His
385

<210> SEQ ID NO 187
<211> LENGTH: 387
```

<212> TYPE: PRT
<213> ORGANISM: artificial sequence
<220> FEATURE:
<223> OTHER INFORMATION: synthetic construct

<400> SEQUENCE: 187

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
                215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Gly Pro Gly Ser Gly Gly Ala Gly Ser Pro Gly Ser Ala Gly Gly Pro
            340                 345                 350

Gly Ser Pro Leu Trp Arg Arg Ile Thr Lys Arg Lys Leu Val Arg Pro
        355                 360                 365

Val Ala Thr Leu Met Trp Tyr Trp Phe Thr Ser Lys Arg His His His
    370                 375                 380
```

His His His
385

<210> SEQ ID NO 188
<211> LENGTH: 382
<212> TYPE: PRT
<213> ORGANISM: artificial sequence
<220> FEATURE:
<223> OTHER INFORMATION: synthetic construct

<400> SEQUENCE: 188

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Gly Pro Ser Gly Gly Ala Gly
                325                 330                 335

Ser Pro Gly Ser Ala Gly Gly Pro Gly Ser Glu Pro Gly Arg Met Leu
            340                 345                 350

Ser Arg Ile Leu Arg Met Phe Val Arg Ile Leu Lys Arg Glu Arg Leu
    355                 360                 365

Ser Gln Val Arg Gly Leu Phe Val His His His His His His
    370                 375                 380

<210> SEQ ID NO 189
<211> LENGTH: 383
<212> TYPE: PRT
<213> ORGANISM: artificial sequence
<220> FEATURE:
<223> OTHER INFORMATION: synthetic construct

<400> SEQUENCE: 189

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Gly Pro Glu Pro Glu Gly Pro Gly Ser
                325                 330                 335

```
Gly Gly Ala Gly Ser Pro Gly Ser Ala Gly Pro Gly Ser Arg Met
                340                 345                 350

Leu Ser Arg Ile Leu Arg Met Phe Val Arg Ile Leu Lys Arg Glu Arg
            355                 360                 365

Leu Ser Gln Val Arg Gly Leu Phe Val His His His His His His
        370                 375                 380
```

<210> SEQ ID NO 190
<211> LENGTH: 390
<212> TYPE: PRT
<213> ORGANISM: artificial sequence
<220> FEATURE:
<223> OTHER INFORMATION: synthetic construct

<400> SEQUENCE: 190

```
Met Ala Phe Phe Asp Leu Pro Leu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320
```

Leu Phe Glu Lys Gly Glu Pro Glu Pro Glu Gly Pro Gly Ser
                325                 330                 335

Gly Gly Ala Gly Ser Pro Gly Ser Ala Gly Gly Pro Gly Ser Glu Pro
            340                 345                 350

Glu Pro Glu Pro Glu Leu Arg Phe Leu Ala Arg Arg Phe Leu Lys Leu
        355                 360                 365

Arg Arg Ala Arg Lys Trp Trp Asn Ala Trp Lys Val Trp Val Thr Arg
370                 375                 380

His His His His His His
385                 390

<210> SEQ ID NO 191
<211> LENGTH: 391
<212> TYPE: PRT
<213> ORGANISM: artificial sequence
<220> FEATURE:
<223> OTHER INFORMATION: synthetic construct

<400> SEQUENCE: 191

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

```
Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Pro Glu Pro Glu Gly Pro Gly Ser Gly Gly Ala Gly Ser Pro Gly Ser
            340                 345                 350

Ala Gly Gly Pro Gly Ser Leu Arg Phe Leu Ala Arg Phe Leu Lys
                355                 360                 365

Leu Arg Arg Ala Arg Lys Trp Trp Asn Ala Trp Lys Val Trp Val Thr
370                 375                 380

Arg His His His His His His
385                 390

<210> SEQ ID NO 192
<211> LENGTH: 426
<212> TYPE: PRT
<213> ORGANISM: artificial sequence
<220> FEATURE:
<223> OTHER INFORMATION: synthetic construct

<400> SEQUENCE: 192

Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
                20                  25                  30

Glu Glu Leu Arg Gln Val Glu Ala Glu Pro Thr Leu Glu Ser Tyr Asp
            35                  40                  45

Tyr Pro Val Lys Gly Val Lys Val Tyr Arg Leu Thr Tyr Gln Ser Phe
50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
            180                 185                 190

Leu Ser Asp Ile Pro Lys Val Val Ala Asp Tyr Pro Tyr Leu Ser
        195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255
```

```
Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
        275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Leu Ser Thr
305                 310                 315                 320

Gly Pro Gly Ser Gly Gly Ala Gly Ser Pro Gly Ser Ala Gly Gly Pro
                325                 330                 335

Gly Ser Pro Ser Ala Gln Ser Gln Leu Pro Asp Lys His Ser Gly Leu
            340                 345                 350

His Glu Arg Ala Pro Gln Arg Tyr Gly Pro Glu Pro Glu Pro Glu Pro
        355                 360                 365

Glu Pro Ile Pro Glu Pro Lys Glu Ala Pro Val Val Ile Glu Lys
    370                 375                 380

Pro Lys Pro Lys Pro Lys Pro Lys Pro Pro Ala His Asp His
385                 390                 395                 400

Lys Asn Gln Lys Glu Thr His Gln Arg His Ala Ala Gly Ser Gly Gly
                405                 410                 415

Gly Gly Ser Pro His His His His His His
            420                 425

<210> SEQ ID NO 193
<211> LENGTH: 372
<212> TYPE: PRT
<213> ORGANISM: artificial sequence
<220> FEATURE:
<223> OTHER INFORMATION: synthetic construct

<400> SEQUENCE: 193

Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
            180                 185                 190
```

Leu Ser Asp Ile Pro Lys Val Val Ala Asp Tyr Pro Tyr Leu Ser
        195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
                260                 265                 270

Pro Pro Ser Thr Val Phe Ala Ala Tyr Asn His Leu Glu Thr Asp Lys
                275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Leu Ser Thr
305                 310                 315                 320

Gly Pro Gly Ser Gly Gly Ala Gly Ser Pro Gly Ser Ala Gly Gly Pro
                325                 330                 335

Gly Ser Asp Pro Thr Lys Pro Pro Arg Thr Pro Thr Ala Asn Thr Ser
                340                 345                 350

Arg Pro His His Asn Phe Gly Ser Gly Gly Gly Ser Pro His His
                355                 360                 365

His His His His
    370

<210> SEQ ID NO 194
<211> LENGTH: 429
<212> TYPE: PRT
<213> ORGANISM: artificial sequence
<220> FEATURE:
<223> OTHER INFORMATION: synthetic construct

<400> SEQUENCE: 194

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
                20                  25                  30

Ala Glu Ala Arg Gln Ala Gly Gly Glu Val Ser Ile Val Gln Ala Gln
            35                  40                  45

Thr Thr Leu Lys Ala Val Gln Ser Phe Asp Val Thr Phe Pro Gly Tyr
        50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

```
Pro Glu Arg Ile Ala Val Cys Gly Asp Ser Gln Gly Gly Ile Ser
            180                 185                 190

Leu Ala Val Gly Gly Ile Asp Pro Arg Val Lys Ala Val Met Pro Asp
            195                 200                 205

Val Pro Phe Leu Cys Asp Phe Pro Arg Ala Val Gln Thr Ala Val Arg
210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
                260                 265                 270

Glu Val Cys Pro Pro Ser Thr Val Tyr Gly Ala Phe Asn Ala Tyr Ala
                275                 280                 285

Gly Glu Lys Thr Ile Thr Glu Tyr Glu Phe Asn Asn His Glu Gly Gly
            290                 295                 300

Gln Gly Tyr Gln Glu Arg Gln Gln Met Thr Trp Leu Ser Arg Leu Phe
305                 310                 315                 320

Gly Val Gly Gly Pro Gly Ser Gly Ala Gly Ser Pro Gly Ser Ala
                325                 330                 335

Gly Gly Pro Gly Ser Pro Ser Ala Gln Ser Gln Leu Pro Asp Lys His
            340                 345                 350

Ser Gly Leu His Glu Arg Ala Pro Gln Arg Tyr Gly Pro Glu Pro Glu
                355                 360                 365

Pro Glu Pro Glu Pro Ile Pro Glu Pro Pro Lys Glu Ala Pro Val Val
370                 375                 380

Ile Glu Lys Pro Lys Pro Lys Pro Lys Pro Lys Pro Lys Pro Pro Ala
385                 390                 395                 400

His Asp His Lys Asn Gln Lys Glu Thr His Gln Arg His Ala Ala Gly
                405                 410                 415

Ser Gly Gly Gly Gly Ser Pro His His His His His
                420                 425

<210> SEQ ID NO 195
<211> LENGTH: 375
<212> TYPE: PRT
<213> ORGANISM: artificial sequence
<220> FEATURE:
<223> OTHER INFORMATION: synthetic construct

<400> SEQUENCE: 195

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110
```

```
Phe Arg Met Asp Thr Arg Gly Gln Gly Ser Asp Trp Ser Val Gly Glu
            115                 120                 125

Thr Ala Asp Pro Val Gly Ser Thr Ser Ser Ile Pro Gly Phe Met Thr
        130                 135                 140

Arg Gly Val Leu Asp Lys Asn Asp Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320

Gly Val Gly Gly Pro Gly Ser Gly Gly Ala Gly Ser Pro Gly Ser Ala
                325                 330                 335

Gly Gly Pro Gly Ser Asp Pro Thr Lys Pro Pro Arg Thr Pro Thr Ala
            340                 345                 350

Asn Thr Ser Arg Pro His His Asn Phe Gly Ser Gly Gly Gly Ser
        355                 360                 365

Pro His His His His His His
    370                 375

<210> SEQ ID NO 196
<211> LENGTH: 418
<212> TYPE: PRT
<213> ORGANISM: artificial sequence
<220> FEATURE:
<223> OTHER INFORMATION: synthetic construct

<400> SEQUENCE: 196

Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
            20                  25                  30

Asn His Gln Phe Glu Phe Glu Leu Ile Glu Lys Asn Leu Ser Ser Lys
        35                  40                  45

Val Val Asn Phe Tyr His Leu Trp Phe Thr Ala Ile Asp Gly Ala Lys
    50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95
```

```
Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
    130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
    210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
        275                 280                 285

Ser Leu Tyr Val Leu Pro Glu Tyr Gly His Glu Tyr Leu Pro Lys Ile
    290                 295                 300

Ser Asp Trp Leu Arg Glu Asn Gln Pro Gly Ser Gly Ala Gly
305                 310                 315                 320

Ser Pro Gly Ser Ala Gly Gly Pro Gly Ser Pro Ser Ala Gln Ser Gln
                325                 330                 335

Leu Pro Asp Lys His Ser Gly Leu His Glu Arg Ala Pro Gln Arg Tyr
            340                 345                 350

Gly Pro Glu Pro Glu Pro Glu Pro Ile Pro Glu Pro Pro Lys
        355                 360                 365

Glu Ala Pro Val Val Ile Glu Lys Pro Lys Pro Lys Pro Lys
    370                 375                 380

Pro Lys Pro Pro Ala His Asp His Lys Asn Gln Lys Glu Thr His Gln
385                 390                 395                 400

Arg His Ala Ala Gly Ser Gly Gly Gly Ser Pro His His His His
                405                 410                 415

His His

<210> SEQ ID NO 197
<211> LENGTH: 363
<212> TYPE: PRT
<213> ORGANISM: artificial sequence
<220> FEATURE:
<223> OTHER INFORMATION: synthetic construct

<400> SEQUENCE: 197

Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
            20                  25                  30

Asn His Gln Phe Glu Phe Glu Leu Ile Glu Lys Asn Leu Ser Ser Lys
```

-continued

```
             35                  40                  45
Val Val Asn Phe Tyr His Leu Trp Phe Thr Ala Ile Asp Gly Ala Lys
         50                  55                  60

Ile His Ala Gln Leu Ile Val Pro Lys Asn Leu Lys Glu Lys Tyr Pro
 65                  70                  75                  80

Ala Ile Leu Gln Phe His Gly Tyr His Cys Asp Ser Gly Asp Trp Val
                 85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
            115                 120                 125

Met Thr Met Lys Gly Leu Ile Val Arg Gly Ile Asp Glu Gly Tyr Glu
            130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
            195                 200                 205

Arg Lys Ala Tyr Glu Leu Gly Ala Glu Glu Ser Ala Phe Glu Glu Leu
            210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
            275                 280                 285

Ser Leu Tyr Val Leu Pro Glu Tyr Gly His Glu Tyr Leu Pro Lys Ile
            290                 295                 300

Ser Asp Trp Leu Arg Glu Asn Gln Gly Pro Gly Ser Gly Gly Ala Gly
305                 310                 315                 320

Ser Pro Gly Ser Ala Gly Gly Pro Gly Ser Asp Pro Thr Lys Pro Pro
                325                 330                 335

Arg Thr Pro Thr Ala Asn Thr Ser Arg Pro His His Asn Phe Gly Ser
            340                 345                 350

Gly Gly Gly Gly Ser Pro His His His His
            355                 360
```